United States Patent
Kato et al.

[11] Patent Number: 5,932,568
[45] Date of Patent: Aug. 3, 1999

[54] 6-METHOXY-1H-BENZOTRIAZOLE-5-CARBOXAMIDE DERIVATIVES AND PHARMACEUTICAL COMPOSITIONS CONTAINING THEM

[75] Inventors: Shiro Kato, Sakai; Yoshimi Hirokawa, Ikoma; Hiroshi Yamazaki, Kadoma; Toshiya Morie, Matsubara; Naoyuki Yoshida, Sakai, all of Japan

[73] Assignee: Dainippon Pharmaceutical Co., Ltd., Osaka, Japan

[21] Appl. No.: 08/849,415

[22] PCT Filed: Nov. 13, 1995

[86] PCT No.: PCT/JP95/02310

§ 371 Date: May 21, 1997

§ 102(e) Date: May 21, 1997

[87] PCT Pub. No.: WO96/16059

PCT Pub. Date: May 30, 1996

[30] Foreign Application Priority Data

Nov. 21, 1994 [JP] Japan .................................. 6-312673

[51] Int. Cl.[6] ........................ A61K 31/55; C07D 401/12
[52] U.S. Cl. ............................... 514/212; 540/480
[58] Field of Search ............................... 540/480; 514/212

[56] References Cited

FOREIGN PATENT DOCUMENTS 52-83737 7/1977 Japan .
52-100473 8/1977 Japan .
2-104572 4/1990 Japan .

OTHER PUBLICATIONS

Fujisawa Pharmaceutical Co, "Preparation of hexahydrozepine, etc" CA 119:49254, 1992.

*Primary Examiner*—Patricia L. Morris
*Attorney, Agent, or Firm*—Wenderoth, Lind & Ponack, L.L.P.

[57] ABSTRACT

6-Methoxy-1H-benzotriazole-5-carboxamide derivatives which are represented by the formula (I) below:

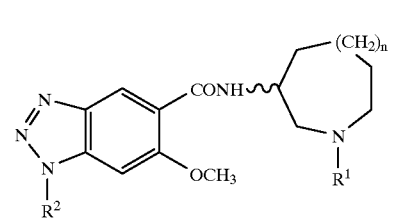

[in which $R^1$ stands for ethyl or cyclopropylmethyl group, $R^2$ stands for hydrogen atom, methyl or ethyl group, n is 1, 2 or 3, and the wavy line ($\sim$) signifies that configuration of the substituents on the carbon atom bound to the N-atom in the amide moiety is racemic (RS) or optically active (R or S)]

or their pharmaceutically acceptable acid addition salts; processes for their preparation; pharmaceutical compositions containing a compound of formula (I) or its pharmaceutically acceptable acid addition salt; and novel intermediates. The compounds of the present invention possess concurrently excellent antiemetic activity and gastrointestinal motility enhancing activity. They furthermore exhibit less central nervous system (CNS) depressant activity and, therefore, are used for treatments and prophylaxis of functional disorders of gastrointestinal tract associated with various diseases and therapeutical treatments, as gastrointestinal motility enhancing agent.

7 Claims, No Drawings

6-METHOXY-1H-BENZOTRIAZOLE-5-CARBOXAMIDE DERIVATIVES AND PHARMACEUTICAL COMPOSITIONS CONTAINING THEM

This application is a 371 of PCT/JP95/02310 filed Nov. 13, 1995.

TECHNICAL FIELD

This invention relates to novel 6-methoxy-1H-benzotriazole-5-carboxamide derivatives which are characterized by their concurrent possession of excellent antiemetic activity and gastrointestinal motility enhancing activity, and less central nervous system (CNS) depressant activity. More particularly the invention relates to 6-methoxy-1H-benzotriazole-5-carboxamide derivatives whose nitrogen atom in the amide moiety (—CONH—) is substituted with 1-substituted-azacyclo-alkan-3-yl group of 7-, 8- or 9-membered ring, processes for their preparation, pharmaceutical compositions containing them, and novel intermediates.

BACKGROUND ART

JP-A 104572/1990 has disclosed that the compounds represented by the following formula [A] exhibit gastrointestinal motility enhancing activity and are useful as antiemetic agent or gastrointestinal motility enhancing agent:

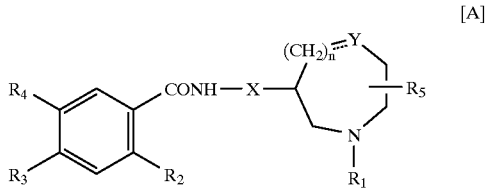

[in which $R_1$ signifies lower alkyl, or optionally substituted aryl (lower) alkyl, $R_2$ signifies hydroxy, alkoxy, alkenyloxy, cycloalkyloxy or substituted alkoxy (the substituent being halogen, hydroxy or oxo), $R_3$ signifies amino, disubstituted amino or acylamino, $R_4$ signifies halogen, or $R_3$ and $R_4$ may together form —NH—N=N—, $R_5$ signifies hydrogen or lower alkyl, X signifies single bond or lower alkylene, Y signifies single bond or a group expressed by —CH$_2$—, —O—, —S—, —SO—, —SO$_2$— or —NR$_6$—, where $R_6$ signifies lower alkyl or optionally substituted aryl (lower) alkyl; or may form ethylene together with $R_1$, n is 0 or 1, and the broken line signifies a double bond which may be present when Y is —CH$_2$— and n is 0, provided:
(i) when Y is —NR$_6$— or a single bond, n is 0;
(ii) when Y is —O—, n is 1;
(iii) when Y is a single bond or —CH$_2$— and n is 0, $R_1$ is an optionally substituted aryl (lower) alkyl; and
(iv) when n is 0, X signifies a lower alkylene].

Said JP-A-104572/1990, however, contains no specific disclosure about the compounds of the present invention which are represented by the later-appearing formula (I) which concurrently possess 1H-benzotriazole skelton and a nitrogen-containing 7-, 8- or 9-membered aliphatic ring, in particular, their optically active compounds and their pharmacological activities of optically active compounds.

JP-A-83737/1977 discloses that the compounds expressed by the following formula [B] exhibit potent activity of reducing the conditioned avoidance response, the apomorphine-induced stereotyped behavior response and the methamphetamine-induced stereotyped behavior, and hence are useful as CNS depressants, in particular, as anti-psychotic drugs:

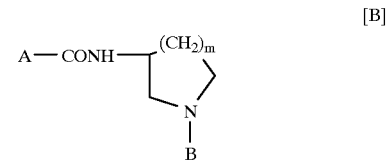

(in which A—CO signifies 4-amino-5-chloro-2-methoxybenzoyl, 5-ethylsulfonyl-2-methoxybenzoyl or 2-methoxy-4,5-azimidobenzoyl group; B signifies allyl or optionally substituted benzyl group; and m is 1 or 2).

Furthermore, JP-A-100473/1977 discloses the compounds represented by the formula [C] below:

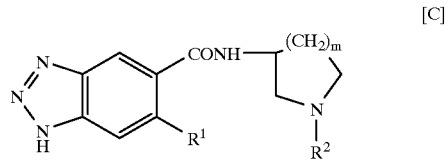

(in which $R^1$ signifies a lower alkoxy, $R^2$ signifies an optionally substituted benzyl, and m is 1 or 2).

In these compounds represented by above formula [B] or [C], however, the ring bound to the amide moiety (—CONH—) is 5- or 6-membered, and the ring-constituting nitrogen atom is substituted with allyl or benzyl group, and in those points differ from the structure of the compounds represented by the later-appearing formula (I) of the present invention. Moreover, their pharmacological activity again differs from those of the compounds of the present invention.

On the other hand, 4-amino-5-chloro-N-[2-(diethylamino)ethyl]-2-methoxybenzamide [generic name: metoclopramide; cf. Merck Index, 11th ed. 6063 (1989)] is known as having antiemetic activity and gastrointestinal motility enhancing activity concurrently, and has been used of old for treatments and prophylaxis of functional disorders of gastrointestinal tract, which are associated with various diseases and therapeutical treatments, as gastrointestinal motility enhancing agent. Metoclopramide, however, possesses CNS depressant activity derived from its dopamine $D_2$ receptor antagonistic activity, which is a drawback for its clinical use. Accompanying the increasing complexity of life in human society and population of aging people, patients suffering from symptoms associated with gastrointestinal dysfunctions also are increasing, and for their treatments development of a compound or compounds exhibiting less CNS depressant activity while having concurrently excellent antiemetic activity and gastrointestinal motility enhancing activity are in demand.

DISCLOSURE OF INVENTION

We have made extensive investigations and found that 6-methoxy-1H-benzotriazole-5-carboxamide derivatives whose nitrogen atom in the amide moiety (—CONH—) is substituted with 1-substituted-azacycloalkan-3-yl group of 7-, 8- or 9-membered ring, in particular, (R)-6-methoxy-1H-benzotriazole-5-carboxamide derivatives whose configuration is R, concurrently possess excellent antiemetic activity and gastrointestinal motility enhancing activity and nevertheless exhibit surprisingly less CNS depressant activity. The present invention is thus completed.

An object of the present invention is to provide novel 6-methoxy-1H-benzotriazole-5-carboxamide derivatives, in particular, (R)-6-methoxy-1H-benzotriazole-5-carboxamide derivatives having R-configuration, which concurrently possess excellent antiemetic activity and gastrointestinal motility enhancing activity. Another object of the invention is to provide processes for preparing said compounds. A further object of the invention is to provide pharmaceutical compositions containing said compounds. A still another object of the invention is to provide novel intermediates which are useful for making the compounds of the invention. These and other objects and advantages of the invention should be clear to those skilled in the art upon reading the following descriptions.

According to the invention, 6-methoxy-1H-benzotriazole-5-carboxamide derivatives represented by the following formula (I), their pharmaceutically acceptable acid addition salts and pharmaceutical compositions containing them are provided:

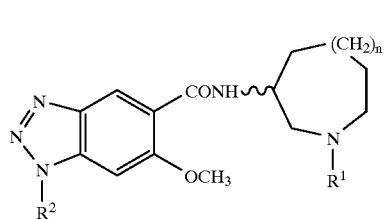

[in which $R^1$ stands for ethyl or cyclopropylmethyl group,
$R^2$ stands for hydrogen atom, methyl or ethyl group,
n is 1, 2 or 3, and
the wavy line (⌇) signifies that configuration of the substitutents on the carbon atom bound to the N-atom in the amide moiety is racemic (RS) or optically active (R or S)].

The invention also provides the compounds represented by the following formula (II) and their acid addition salts, which are useful as the intermediates for preparing the compounds of formula (I) in which $R^2$ is hydrogen atom:

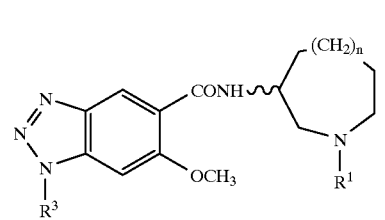

[in which $R^3$ stands for an amino-protective group; and $R^1$, n and the wavy line are the same as defined in above formula (I)].

The invention furthermore provides the intermediates of the following formula (IV) and their acid addition salts, which are useful for making the compounds of formula (I) of the present invention:

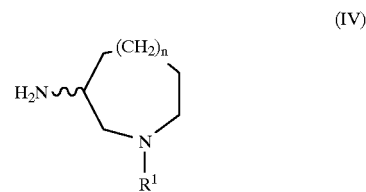

[in which $R^1$, n and the wavy line are the same as defined in formula (I)], in particular, the compounds of the following formula (IVa) and their acid addition salts, which are useful as intermediates for making the compounds of formula (I) whose configuration is R:

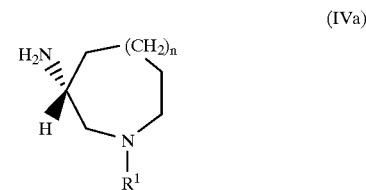

(in which $R^1$ and n are the same as defined in formula (I)).

The pharmaceutically acceptable acid addition salts of the compounds of formula (I) include, for example, inorganic acid salts harmless to human body, such as hydrochloride, hydrobromide, hydroiodide, sulfate, phosphate, etc.; and organic acid salts harmless to human body such as oxalate, maleate, fumarate, lactate, malate, citrate, tartrate, benzoate, methanesulfonate, etc. The compounds of formula (I) and their acid addition salts may be present in the form of hydrate or solvate, which are also included within the scope of the present invention. More specifically, for example, 1/4 hydrate, 1/2 hydrate, monohydrate, 3/2 fumarate- 1/4 hydrate, 3/2 fumarate.1/2 hydrate, difumarate.1/2 hydrate, etc. may be named.

Acid addition salts of the intermediates of the present invention as represented by formulae (II) and (IV) or (IVa) include, for example, those pharmaceutically acceptable acid addition salts as named above. The compounds of formulae (II) and (IV) or (IVa) and their acid addition salts may be present in the form of hydrate or solvate, which are also included in the scope of the present invention.

When the compounds of formula (I) and their acid addition salts are obtained in crystalline form, different kinds of polymorphism may be present, which are also within the scope of the present invention.

The compounds of formula (I) in which $R^2$ is hydrogen is considered to be present in the form of tautomers in which 6-methoxy-1H-benzotriazole moiety is represented by the formula (I') or (I'') below:

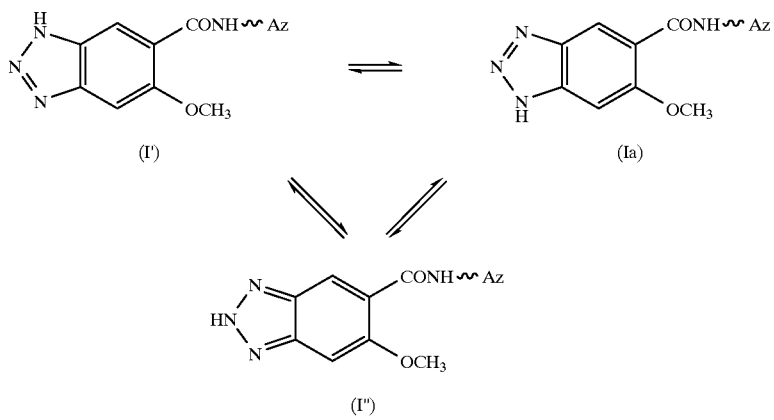

[in which Az stands for a group of formula [D] below:

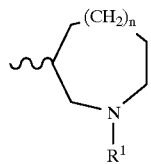

[D]

(in which R¹, n and the wavy line are the same as previously defined)].

These tautomers are also included within the scope of the present invention.

The structure of the compounds of the present invention, whose $R^2$ in formula (I) is a hydrogen atom, will be represented by formula (Ia), and their chemical name also will be based on said structure.

Those compounds whose $R^2$ in formula (I) is methyl or ethyl group do not exhibit such tautomerism as above.

The term, "halogen", as used in this specification cation signifies fluorine, chlorine, bromine or iodine. Specific examples of "alkyl groups" include methyl, ethyl, propyl and isopropyl. Specific examples of "alkoxy groups" include methoxy, ethoxy, propoxy and isopropoxy. Specific examples of "lower alkanoyl groups" are acetyl and propionyl, and those of "lower alkoxycarbonyl groups" are methoxycarbonyl and ethoxycarbonyl. As "optionally substituted benzyl", those benzyl groups whose phenyl moiety is optionally substituted with one or two of above-mentioned halogen atoms, $C_1$–$C_3$ alkyl groups and $C_1$–$C_3$ alkoxy groups are preferred, specific examples including benzyl, 2-, 3- or 4-chlorobenzyl, 3-bromobenzyl, 4-fluorobenzyl, 2,4- or 3,4-dichlorobenzyl, 4-methylbenzyl, 2-, 3- or 4-methoxybenzyl, etc. "Optionally substituted benzyloxycarbonyl" are those whose phenyl moiety is optionally substituted with one or two of above-mentioned halogen atoms, $C_1$–$C_3$ alkyl groups, $C_1$–$C_3$ alkoxy groups, nitro group, etc., specific examples including benzyloxycarbonyl, 4-chlorobenzyloxycarbonyl, 4-bromobenzyloxycarbonyl, 2,4-dichlorobenzyloxycarbonyl and 4-methoxybenzyloxycarbonyl. "Amino-protective group" signifies such protective groups which can be eliminated upon hydrolysis or hydrogenolysis, examples of which including above-explained lower alkanoyl, trifluoroacetyl, lower alkoxycarbonyl, optionally substituted benzyl and optionally substituted benzyloxycarbonyl groups, benzyl and acetyl being the particularly preferred.

As preferred examples of the compounds of the present invention which are represented by formula (I), the following compounds and their pharmaceutically acceptable acid addition salts may be given:

N-(1-ethyl-1H-hexahydroazepin-3-yl)-6-methoxy-1H-benzotriazole-5-carboxamide, (R)-N-(1-ethyl-1H-hexahydroazepin-3-yl)-6-methoxy-1H-benzotriazole-5-carboxamide, N-(1-ethyl-1H-hexahydroazepin-3-yl)-6-methoxy-1-methyl-1H-benzotriazole-5-carboxamide, (R)-N-(1-ethyl-1H-hexahydroazepin-3-yl)-6-methoxy-1-methyl-1H-benzotriazole-5-carboxamide, (R)-1-ethyl-N-(1-ethyl-1H-hexahydroazepin-3-yl)-6-methoxy-1H-benzotriazole-5-carboxamide, N-(1-ethyl-1H-heptahydroazocin-3-yl)-6-methoxy-1H-benzotriazole-5-carboxamide, N-(1-ethyl-1H-heptahydroazocin-3-yl)-6-methoxy-1-methyl-1H-benzotriazole-5-carboxamide, N-(1-ethyl-1H-octahydroazonin-3-yl)-6-methoxy-1H-benzotriazole-5-carboxamide, (R)-N-(1-cyclopropylmethyl-1H-hexahydroazepin-3-yl)-6-methoxy-1H-benzotriazole-5-carboxamide, and (R)-N-(1-cyclopropylmethyl-1H-hexahydroazepin-3-yl)-6-methoxy-1-methyl-1H-benzotriazole-5-carboxamide.

In particular, the compounds of Formula (I) in which $R^1$ is ethyl and $R^2$ is hydrogen or methyl are more preferably used.

In respect of the configuration, those compounds of formula (I) in which the configuration of the substituents on the carbon atom bound to the N-atom in the amide moiety is racemic (RS) or optically active (R) are preferred, in particular, the latter, are more preferred.

In respect of the azacycloalkane ring, it can suitably be any of 7-, 8- or 9-membered ring, while 7-membered ring is particularly preferred, i.e., the compounds of formula (I) in which n is 1 are preferred.

Of the above-mentioned compounds, those particularly preferred are the following and their pharmaceutically acceptable acid addition salts:

(R)-N-(1-ethyl-1H-hexahydroazepin-3-yl)-6-methoxy-1H-benzotriazole-5-carboxamide (later identified as Compound 7), and (R)-N-(1-ethyl-1H-hexahydroazepin-3-yl)-6-methoxy-1-methyl-1H-benzotriazole-5-carboxamide (later identified as Compound 2)

In addition to the previously listed compounds, the following compounds and their pharmaceutically acceptable acid addition salts may be given as specific examples of other preferred compounds included within the present invention:

(R)-N-(1-ethyl-1H-heptahydroazocin-3-yl)-6-methoxy-1H-benzotriazole-5-carboxamide, (R)-N-(1-ethyl-1H-octahydroazonin-3-yl)-6-methoxy-1H-benzotriazole-5-carboxamide, (R)-N-(1-ethyl-1H-heptahydroazocin-3-yl)-6-methoxy-1-methyl-1H-benzotriazole-5-carboxamide, and (R)-N-(1-ethyl-1H-octahydroazonin-3-yl)-6-methoxy-1-methyl-1H-benzotriazole-5-carboxamide.

The compounds of the present invention can be prepared, for example, through the following processes.

Process (a)

The compounds of formula (I) can be prepared by reacting the compounds represented by formula (III) below:

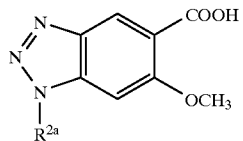

(III)

(in which $R^{2a}$ stands for hydrogen, methyl, ethyl, or an amino-protective group)

or their reactive derivatives, with the compounds represented by formula (IV) below:

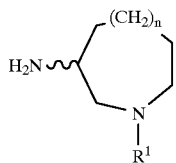

(IV)

[in which $R^1$, n and the wavy line are the same as defined in formula (I)].

When, in this case, $R^{2a}$ in formula (III) is an amino-protective group, the reaction product should further be subjected to hydrolysis or hydrogenolysis to convert $R^{2a}$ to hydrogen atom, to form the compound of formula (I).

The reaction of compounds of formula (III) with those of formula (IV) can be performed by well known amidation reaction.

Examples of reactive derivatives of compounds of formula (III) include lower alkyl esters (inter alia, methyl ester), active esters, acid anhydrides and acid halides (inter alia, acid chloride) [when a compound of formula (III) in which $R^{2a}$ is hydrogen atom is used, acid anhydrides and acid halides are excluded]. Specific examples of active esters include p-nitrophenyl ester, pentachlorophenyl ester, N-hydroxy succinimide ester, N-hydroxyphthalimide ester, 1-hydroxybenzotriazole ester, 8-hydroxyquinoline ester, 2-hydroxyphenyl ester and 2-hydroxy-4,5-dichlorophenyl ester. As acid anhydride, symmetric acid anhydride or mixed acid anhydride are used, specific examples of the latter including those mixed with alkyl chloroformates such as ethyl chloroformate or isobutyl chloroformate; those mixed with aralkyl chloroformates such as benzyl chloroformate; those mixed with aryl chloroformates such as phenyl chloroformate; and those mixed with alkanoic acids such as isovaleric acid and pivalic acid.

As amino-protective groups which may serve as $R^{2a}$, such protective groups which can be eliminated upon hydrolysis or hydrogenolysis can be used, examples of which including lower alkanoyl, trifluoroacetyl, lower alkoxycarbonyl, optionally substituted benzyl and optionally substituted benzyloxycarbonyl, acetyl being particularly preferred.

When the compounds per se of formula (III) are used, the reaction can be carried out in the presence of a condensing agent, such as N,N'-dicyclohexylcarbodiimide, 1-ethyl-3-(3-dimethylaminopropyl) carbodiimide hydrochloride, N,N'-carbonyldiimidazole, N,N'-carbonyldisuccinimide, 1-ethoxycarbonyl-2-ethoxy-1,2-dihydroquinoline, diphenylphosphorylazide and propane-phosphonic anhydride. When N,N'-dicylohexylcarbodiimide or 1-ethyl-3-(3-dimethylaminopropyl) carbodiimide hydrochloride is used as the condensing agent, N-hydroxysuccinimide, 1-hydroxybenzotriazole, 3-hydroxy-1,2,3-benzotriazin-4(3H)-one, N-hydroxy-5-norbornene-2,3-dicarboxyimide, or the like may be added to the reaction mixture.

The reaction of such compounds of formula (III) or their reactive derivatives with compounds of formula (IV) is conducted either in a solvent or in the absence of solvent. Useful solvents should be suitably selected according to the kind of starting compound, etc., which include: aromatic hydrocarbons such as benzene, toluene and xylene; ethers such as diethyl ether, tetrahydrofuran and dioxane; halogenated hydrocarbons such as methylene chloride and chloroform; alcohols such as ethanol and isopropyl alcohol; ethyl acetate, acetone, acetonitrile, dimethylformamide, dimethylsulfoxide, ethylene glycol, and water. These solvents may be used each singly or as a mixture of more than one kind of solvent. This reaction is carried out in the presence of a base, if required, specific examples of the base including alkali hydroxide such as sodium hydroxide and potassium hydroxide; alkali carbonate such as sodium carbonate and potassium carbonate; alkali bicarbonate such as sodium bicarbonate and potassium bicarbonate; and organic base such as triethylamine, tributylamine, diisopropylethylamine and N-methylmorpholine. An excess amount of a compound of formula (IV) may also function as the base. The reaction temperature differs depending on the kind of the starting compounds, etc., but normally ranges from about −30° C. to about 200° C., preferably from about −10° C. to about 150° C.

When compounds of formula (III) in which $R^{2a}$ is an amino-protective group, e.g., lower alkanoyl, trifluoroacetyl, lower alkoxycarbonyl or optionally substituted benzyloxycarbonyl, are reacted with compounds of formula (IV) to form compounds of formula (I) in which $R^2$ is the corresponding protective group, the products can be hydrolyzed to be converted to the compounds of formula (I) in which $R^2$ is hydrogen. The hydrolyzing reaction can be carried out by the method known per se, for example, by contacting the product with water in a suitable solvent under acidic or basic conditions. As the solvent, for example, alcohols such as methanol, ethanol, isopropyl alcohol or the like, dioxane, water, or their liquid mixtures may be used. Specific examples of the acid to create an acidic condition include mineral acids such as hydrochloric, hydrobromic and sulfuric acids; organic acids such as formic, acetic, propionic and oxalic acids; and silica gel. When a compound of formula (III) in which $R^{2a}$ is an acetyl group is used, use of silica gel readily eliminates the acetyl group to convert the $R^2$ to hydrogen atom. Specific examples of bases to create a basic condition include alkali hydroxide such as sodium or potassium hydroxide; and alkali carbonate such as sodium or potassium carbonate. The reaction temperature is normally in the range of from about 20° C. to about 100° C.

When a compound of formula (III) in which $R^{2a}$ is, among the named examples of amino-protective groups, an optionally substituted benzyl or benzyloxycarbonyl group is reacted with a compound of formula (IV) to form a compound of formula (I) in which $R^2$ is the corresponding protective group, hydrogenolysis of the product can convert such R² to hydrogen. The hydrogenolysis can be carried out by a method known per se, for example, by reacting the product with hydrogen in a suitable solvent in the presence of a catalyst such as palladium-on-carbon, Raney nickel, etc. As the useful solvent, alcohols such as methanol or ethanol, acetic acid, dioxane, tetrahydrofuran, water or their liquid mixtures can be used. The reaction temperature is normally within a range of from about 0° C. to about 80° C. The reaction is carried out under normal or elevated pressure.

Compounds of formula (III) in which $R^{2a}$ is hydrogen or an amino-protective group (lower alkanoyl group, trifluoroacetyl group, lower alkoxycarbonyl group or optionally substituted benzyloxycarbonyl group) and their reactive derivatives can be prepared through the process described in, e.g., JP-A-80858/1976 (U.S. Pat. No. 4,039,672) or processes analogous thereto.

The compounds of formula (III) in which $R^{2a}$ is methyl, ethyl or amino-protective group (optionally substituted benzyl group) can be prepared by a process using 4-chloro-2-methoxy-5-nitrobenzoic acid as the starting material, comprising converting it to a corresponding, adequate amide body using a suitable amine such as propylamine according to the later-appearing step 1 in scheme 4, introducing methyl, ethyl or optionally substituted benzyl group at R² position and reducing the formed product according to the later-appearing steps 2 and 3 in scheme 4, preparing therefrom a corresponding 6-methoxy-1H-benzotriazole-5-carboxamide derivative by the method (b) as described later, and then hydrolyzing the product in the manner known per se.

Specific examples of production processes of the compounds of formula (IV) are as follows.

Those compounds of formula (IV) in which n=1 can be prepared, for example, by the method as illustrated by scheme 1 below.

Scheme 1

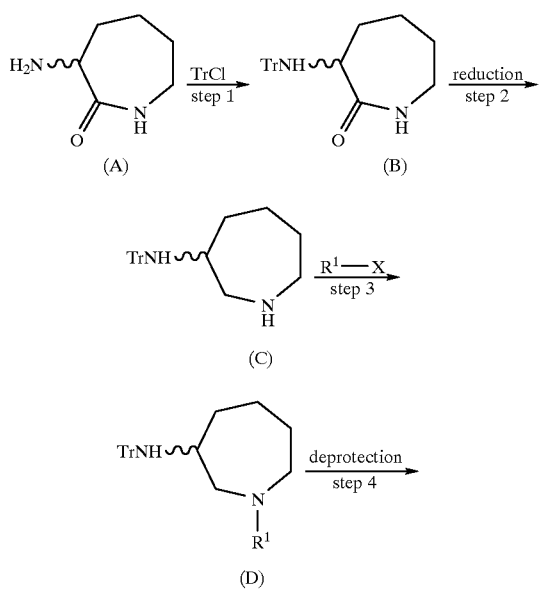

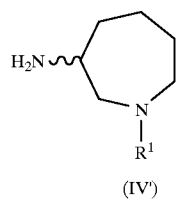

(IV')

[In the above scheme 1, Tr stands for triphenylmethyl group, X stands for a reactive ester residue of alcohol, R¹ is same as previously defined, and the wavy line signifies a racemic or optically active configuration as previously defined].

Step 1:

The reaction between a compound of formula (A) and chlorotriphenylmethane is normally carried out in a suitable solvent, in the presence of a base. Useful solvent and base are same as those named in respect of above process (a). The reaction temperature normally ranges from about −10° C. to about 150° C., preferably from about 0° C. to about 100° C. As the R and S isomers of formula (A) which are the starting compounds, commercial optically active compounds may be used, or commercial racemic compound may be optically resolved, for example, by the method as described in *J. Org. Chem.*, 44, 4841–4847 (1979), or prepared from optically active lysine by, for example, the method as described in *Synthesis*, 35 1978, 614–616. These method of optical resolution or synthesis of optically active compound are themselves well known.

Step 2:

The compounds of formula (C) can be prepared by reducing the compounds of formula (B), using a metal hydride such as diisobutylaluminum hydride, lithium-aluminum hydride, sodium bis(2-methoxyethoxy)aluminum hydride or the like. Specific examples of useful solvents include, for example, ethers such as diethyl ether, tetrahydrofuran, etc.; aromatic hydrocarbons such as benzene, toluene, etc.; and halogenated hydrocarbons such as methylene. chloride, chloroform, etc. The reaction temperature is variable depending on the kind of used metal hydride, while it normally ranges from about −10° C. to about 100° C., preferably from about 0° C. to about 50° C.

Step 3:

The reaction of a compound of formula (C) with an R¹ introducing agent which is expressed by a formula, R¹-X, is normally carried out in a suitable solvent, in the presence of a base. As the reactive ester residue of alcohol, which is expressed by X, for example, halogen atoms such as chlorine, bromine and iodine; lower alkylsulfonyloxy groups such as methanesulfonyloxy; and arylsulfonyloxy groups such as benzenesulfonyloxy may be named. Specific examples of the solvent include: aromatic hydrocarbons such as benzene, toluene; ketones such as acetone, methyl ethyl ketone; ethers such as tetrahydrofuran, dioxane; alcohols such as ethanol, isopropyl alcohol; acetonitrile, chloroform, ethyl acetate, dimethylformamide, dimethylsulfoxide, and their liquid mixtures. Specific examples of useful base are same as those named in respect of above process (a). When X in the R¹-introducing agent (R¹-X) is chlorine or bromine, an alkali metal iodide such as sodium iodide or potassium iodide is added for smooth progress of the reaction. The reaction temperature is variable depending on the kind of R¹-introducing agent used, while normally it ranges from about 0° C. to about 200° C., preferably from about 80° C. to about 150° C.

Step 4:

The reaction of this step is normally carried out in a suitable solvent, in the presence of a mineral acid such as diluted hydrochloric acid, diluted sulfuric acid, or the like. Specific examples of useful solvent include alcohols such as methanol, ethanol; ethers such as diethyl ether, tetrahydrofuran; acetone, acetonitrile, ethylene glycol and liquid mixtures of the foregoing. The reaction temperature varies depending on the kind of the starting compound used, while normally it ranges from about 0° C. to about 100° C.

Compounds of formula (IV') can also be prepared when the order of step 2 reductive reaction and step 3 $R^1$-introducing reaction in above scheme 1 is reversed. That is, introduction of $R^1$ into a compound of formula (B) (step 2') and following reduction (step 3') can lead to a corresponding compound of formula (D). In the reaction of such a step 2', use of a strong base such as sodium hydride instead of the base as described in respect of process (a) is preferred. Furthermore, in the reduction reaction 3', use of, for example, sodium bis(2-methoxyethoxy)aluminum hydride is preferred.

The compounds of formula (IV) in which n is 2 or 3 can be prepared, for example, by the method as illustrated by scheme 2 below:

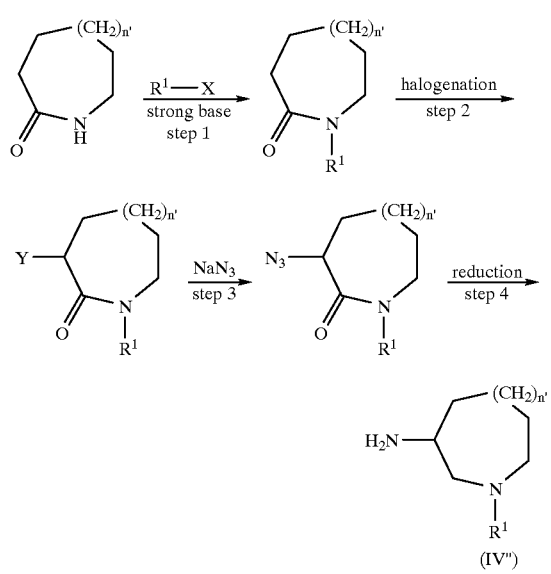

Scheme 2

(in which Y stands for a halogen atom, n' is 2 or 3, and $R^1$ and X are the same as previously defined).

Step 1 in above scheme 2 can be carried out in the manner similar to step 2', a modified process of the one illustrated by scheme 1, using as the starting material commercial 2-azacyclooctanone or 2-azacyclononanone, for example. The halogenation of step 2 can be effected by, for example, following the method as described in J. Am. Chem. Soc., 80, 6233–6237 (1958). Steps 3 and 4 may follow, for example, the method as described in Helv. Chim. Acta, 41, 181–188 (1958).

Compounds of formula (IV) can also be prepared by the method as illustrated by scheme 3 below:

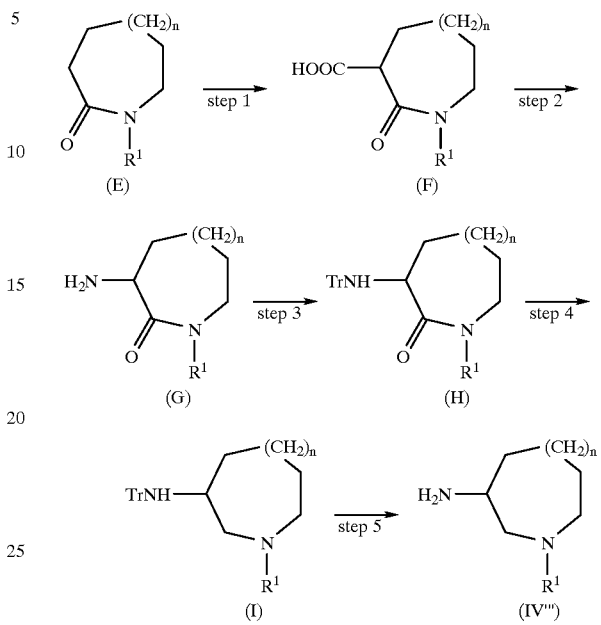

Scheme 3

(in which $R^1$, Tr and n are the same as previously defined).

Step 1 in above scheme 3 can be carried out in a suitable solvent, by causing a compound of formula (E) to generate anion under the action of a strong base, and then reacting the same with dry ice.

The conversion of carboxyl group to amino group in step 2 can be effected by reacting a compound of formula (F) with ethyl chloroformate and sodium azide in a suitable solvent, then heating the resulting acylazide, and subjecting the isocyanate product to the action of an acid. Triphenylmethylation of step 3, reduction of step 4 and deprotection of triphenylmethyl group of step 5 can be carried out in the manner similar to the steps 1, 2 and 4 of scheme 1, respectively.

The starting compounds of formula (E) can be prepared by the method of step 1 of scheme 2, using as the starting material ε-caprolactam, 2-azacyclooctanone or 2-azacyclononanone.

According to the process as illustrated by scheme 1, the configuration of starting compound (A) is retained in the final product of formula (IV'). Whereas, the final products (IV") or (IV''') prepared by the processes of scheme 2 or scheme 3 are racemic. Racemic compounds of formula (IV) can be resolved into two optical isomers through the procedures known per se. For example, such a compound of formula (IV) is treated with an optically active acid to form salts or amides of diastereomers which are separated by fractional recrystallization or column chromatography, and then converted to free bases.

The compounds of above formula (IV) are novel. Those which are represented by the following formula (IVa) whose configuration is R,

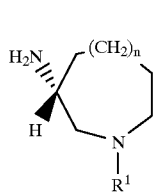

(IVa)

(in which R¹ and n are the same as previously defined), are useful as novel intermediates for the compounds of formula (I) having R-configuration, the compounds represented by formula (IVb) below:

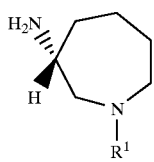

(IVb)

(in which R¹ is the same as previously defined) being particularly preferred.

Process (b)

The compounds of formula (I) may be prepared by diazotizing the compounds of formula (V) below:

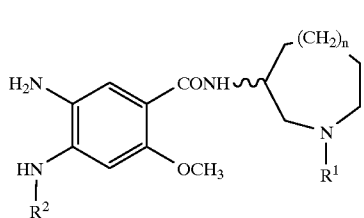

(V)

(in which R¹, R², n and the wavy line are the same as previously defined) to form benzotriazole ring.

The ring-closing reaction (benzotriazole ring-forming reaction) to form compounds of formula (I) by diazotizing compounds of formula (V) is carried out under the diazotizing conditions conventionally employed for aromatic amines. As diazotization agents, for example, alkyl esters of nitrous acid such as sodium nitrite, tert.-butyl nitrite and isoamyl nitrite may be used. The ring-closure using nitrous acid is normally carried out by first adding an excess amount of a mineral acid (e.g., hydrochloric acid) or an organic acid (e.g., acetic acid) to an aqueous solution of a compound of formula (V) or an acid addition salt thereof, and then adding an aqueous solution of sodium nitrite. The reaction temperature is normally in the range of from about −20° C. to about 60° C., preferably from about 0° C. to about 25° C. Whereas, the ring-closure using a nitrous acid alkyl ester is normally carried out i n a suitable solvent, by reacting a compound of formula (V) or an acid addition salt thereof (e.g., hydrochloride, acetate) with nitrous acid alkyl ester. Examples of suitable solvent include methanol, acetic acid, acetic acid-dioxane, 1,2-dimethoxyethane, tetrahydrofuran, acetone and methylene chloride. The reaction temperature is normally within a range of from about 0° C. to about 100° C., preferably from about 30° C. to about 80° C.

The starting compounds represented by formula (V) can be prepared, for example, by the process as illustrated by scheme 4 below.

Scheme 4

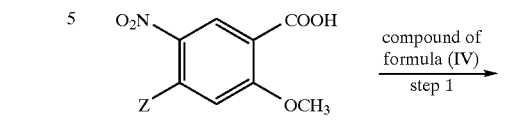

(J)

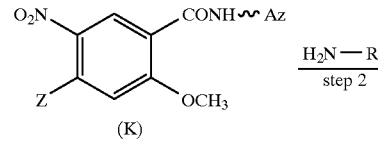

(K)

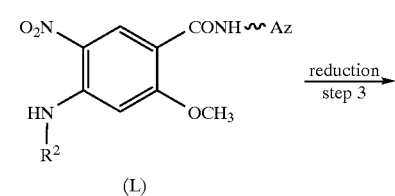

(L)

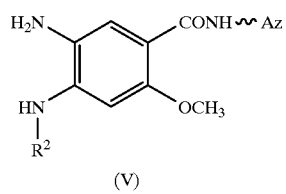

(V)

(in which Z stands for a halogen atom, and R², Az and the wavy line are the same as previously defined).

Step 1:

The reaction of compounds of formula (J) or their reactive derivatives with compounds of formula (IV) can be carried out in the manner similar to the process (a). The starting compounds of formula (J) can be prepared, for example, by the method as described in *Helv. Chim. Acta*, 40, 369–372 (1957).

Step 2:

The reaction of compounds of formula (K) with those expressed by a formula, H₂N—R², is carried out without using a solvent or in an adequate solvent. Examples of useful solvent include alcohols such as methanol and ethanol; dimethylformamide, dimethylsulfoxide, and water. The reaction temperature is normally within a range of from about 0° C. to about 150° C.

Step 3:

Reduction of compounds of formula (L) is performed according to the conventional method. For example, a compound of formula (L) can be treated in a suitable solvent, with a reducing agent. Specific examples of useful reducing agents include combination of metals (e.g., tin, zinc, iron) or metal salts (e.g., stannous chloride) with acids (e.g., hydrochloric acid, acetic acid), while iron or stannous chloride can be used as a reducing agent by itself. The reduction can also be performed, by hydrogenation of compounds of formula (L) in a suitable solvent, in the presence of a catalyst. Specific examples of the catalyst include palladium-on-carbon, Raney nickel, and platinum oxide. The solvent should be selected according to the kind of reducing agent or reducing means used. Those normally used are alcohols such as methanol and ethanol; ethyl acetate, acetone, acetic acid, dioxane, water or their liquid mixtures. The reaction temperature also is variable depending on the reducing agent or reducing means used in each case, while it is normally within a range of from about 10° C. to about 100° C., and in cases of catalytic reduction a range of from about 10° C. to about 50° C. is preferred.

So formed compounds of formula (V) can be used as the starting material of the production process (b), without isolation and purification.

Process (c)

The compounds of formula (I) in which $R^2$ is a hydrogen atom can also be prepared by hydrogenolysis of the compounds represented by formula (IIa) below:

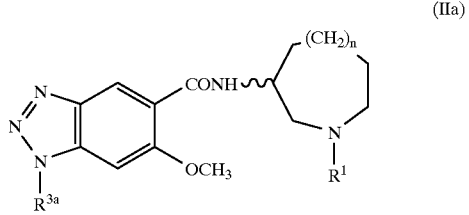

(IIa)

[in which $R^{3a}$ stands for an amino-protective group (e.g., optionally substituted benzyl group or optionally substituted benzyloxycarbonyl group), and $R^1$, n and the wavy line are the same as previously defined].

The hydrogenolysis can be carried out according to the conventional method, for example, by reacting the compounds either with hydrogen in a suitable solvent and in the presence of a catalyst such as palladium-on-carbon, Raney nickel or the like; or with a hydrogen donor (e.g., ammonium formate, cyclohexene) in the presence of a catalyst such as palladium-on-carbon. As the solvent, for example, alcohols such as ethanol and methanol; water, acetic acid, dioxane or tetrahydrofuran is used. The reaction temperature normally ranges from about 0° C. to about 80° C. The reaction is carried out under normal or elevated pressure.

The compounds of formula (IIa) in which $R^{3a}$ is optionally substituted benzyl group can be prepared by the process (b) using as the starting compounds those of formula (V) in scheme 4, in which $R^2$ is, for example, optionally substituted benzyl group. The starting compounds (V) can be prepared by the process as illustrated by the scheme 4. In that case, the reduction reaction of step 3 is preferably conducted using combination of a metal or metal salt with an acid, or iron or stannous chloride.

The compounds of formula (IIa) in which $R^{3a}$ is optionally substituted benzyloxycarbonyl group can be prepared by the process (a) using as the starting compounds those of formula (III) in which $R^{2a}$ is optionally substituted benzyloxycarbonyl group, which in turn can be prepared by, for example, by the method as described in JP-A-80858/1976 (U.S. Pat. No. 4,039,672) or methods analogous thereto.

Process (d)

The compounds of formula (I) in which $R^2$ is a hydrogen atom can also be prepared by hydrolyzing the compounds of formula (IIb) below:

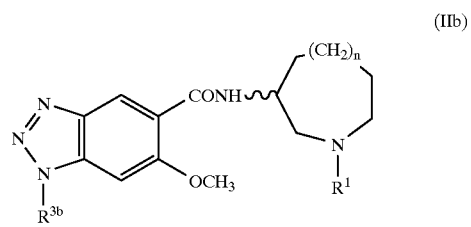

(IIb)

[in which $R^{3b}$ stands for an amino-protective group (e.g., lower al kanoyl, trifluoroacetyl, lower alkoxycarbonyl or optionally substituted benzyloxycarbonyl), and $R^1$, n and the wavy line are the same as previously defined].

The hydrolyzing reaction can be carried out in the manner known per se, for example, by contacting the starting compound (IIb) with water in a suitable solvent, under acidic or basic conditions. As the solvent, for example, alcohols such as methanol, ethanol, isopropyl alcohol and the like; dioxane, water or their mixtures are used. Specific examples of the acid to create the acidic condition include mineral acids such as hydrochloric, hydrobromic and sulfuric acids; organic acids such as formic, acetic, propionic and oxalic acid; and silica gel. When the compound of formula (IIb) has acetyl group as $R^{3b}$, use of silica gel allows ready elimination of the acetyl group and conversion to the compound of formula (I) in which $R^2$ is a hydrogen atom. Specific examples of base to create basic conditions include alkali hydroxide such as sodium or potassium hydroxide; and alkali carbonate such as sodium carbonate, potassium carbonate, etc. The reaction temperature normally ranges from about 20° C. to about 100° C.

The compounds of formula (IIb) which are the intermediates of the present invention can be prepared by the earlier described process (a), using as the starting compounds those of formula (III) in which $R^{2a}$ is a lower alkanoyl, trifluoroacetyl, lower alkoxycarbonyl or optionally substituted benzyloxycarbonyl, which in turn can be prepared by, for example, the method as described in JP-A-80858/1976 (U.S. Pat. No. 4,039,672) or methods analogous thereto.

According to processes (a), (b), (c) and (d), configurations of the starting compounds of formulae (IV), (V), (IIa) and (IIb) are retained in the formed compounds of formula (I). Therefore, it is preferred to prepare compounds of formula (I) having the desired configuration using the starting compounds having the corresponding configuration. Whereas, it is also possible to use a racemic starting compound to obtain a racemic compound of formula (I), which can then be optically resolved by a conventional method.

The compounds prepared by the above processes can be isolated and purified by the conventional techniques such as chromatography, recrystallization, reprecipitation or the like.

The compounds of formula (I) and those of formulae (IIa) and (IIb) are obtained in the form of free base or acid addition salt, depending on the kinds of starting compounds, reaction and treating conditions. The acid addition salts can be converted to free base by treating it with a base such as an alkali carbonate or alkali hydroxide. Whereas, the free bases can be led to acid addition salt form, by treating it with various acids according to the conventional method.

Hereinafter test results of the typical compounds of the present invention and metoclopramide hydrochloride monohydrate (Compound A), a commercial gastrointestinal motility improving agent, are presented and the pharmacological action characteristic of the compounds of the invention is explained.

First, structures and compound numbers of the compounds of the present invention which were used in the pharmacological tests are listed below.

Compound of Example 1 (Compound 1)
N-(1-ethyl-1H-hexahydroazepin-3-yl)-6-methoxy-1-methyl-1H-benzotriazole-5-carboxamide,

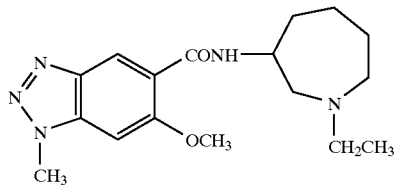

Compound of Example 2 (Compound 2)
(R)-N-(1-ethyl-1H-hexahydroazepin-3-yl)-6-methoxy-1-methyl-1H-benzotriazole-5-carboxamide

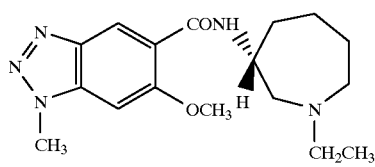

Compound of Example 4 (Compound 4)
1-ethyl-N-(1-ethyl-1H-hexahydroazepin-3-yl)-6-methoxy-1H-benzotriazole-5-carboxamide

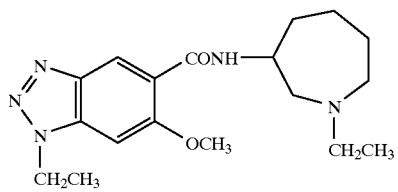

Compound of Example 5 (Compound 5)
(R)-1-ethyl-N-(1-ethyl-1H-hexahydroazepin-3-yl)-6-methoxy-1H-benzotriazole-5-carboxamide

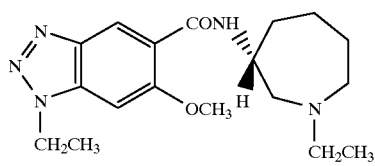

Compound of Example 6 (Compound 6)
N-(1-ethyl-1H-hexahydroazepin-3-yl)-6-methoxy-1H-benzotriazole-5-carboxamide

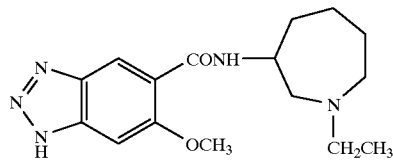

Compound of Example 7 (Compound 7a)
(R)-N-(1-ethyl-1H-hexahydroazepin-3-yl)-6-methoxy-1H-benzotriazole-5-carboxamide

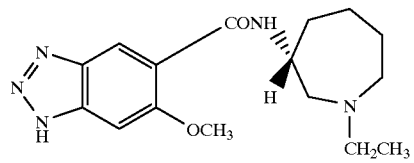

(Compound 7b)
(R)-N-(1-ethyl-1H-hexahydroazepin-3-yl)-6-methoxy-1H-benzotriazole-5-carboxamide.3/2 fumarate Compound of Example 9 (Compound 9)
N-(1-ethyl-1H-heptahydroazocin-3-yl)-6-methoxy-1H-benzotriazole-5-carboxamide

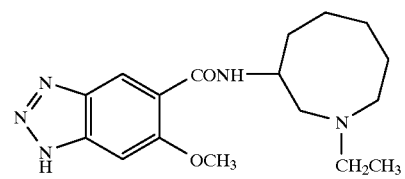

Compound of Example 10 (Compound 10)
N-(1-ethyl-1H-octahydroazonin-3-yl)-6-methoxy-1H-benzotriazole-5-carboxamide

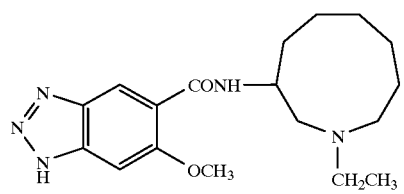

Compound of Example 11 (Compound 11)
N-(1-cyclopropylmethyl-1H-hexahydroazepin-3-yl)-6-methoxy-1H-benzotriazole-5-carboxamide

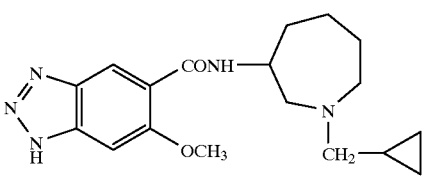

Compound of Example 12 (Compound 12)
(R)-N-(1-cyclopropylmethyl-1H-hexahydroazepin-3-yl)-6-methoxy-1H-benzotriazole-5-carboxamide

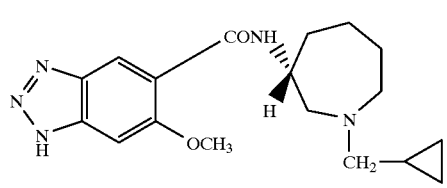

Compound of Example 13 (Compound 13)
(R)-N-(1-cyclopropylmethyl-1H-hexahydroazepin-3-yl)-6-methoxy-1-methyl-1H-benzotriazole-5-carboxamide

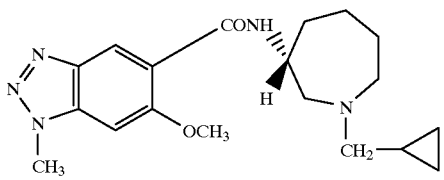

Compound of Example 14 (Compound 14)
N-(1-ethyl-1H-heptahydroazocin-3-yl)-6-methoxy-1-methyl-1H-benzotriazole-5-carboxamide

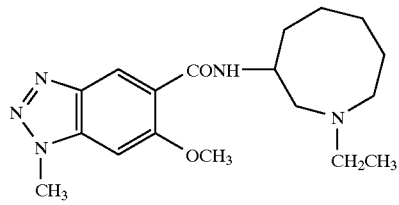

Compound of Example 15 (Compound 15)
N-(1-ethyl-1H-octahydroazonin-3-yl)-6-methoxy-1-methyl-1H-benzotriazole-5-carboxamide

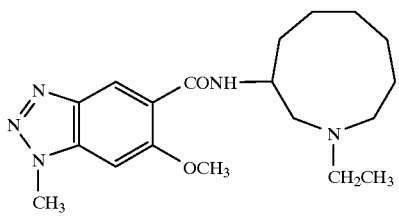

Compound of Example 3 (Compound 3)
(S)-N-(1-ethyl-1H-hexahydroazepin-3-yl)-6-methoxy-1-methyl-1H-benzotriazole-5-carboxamide

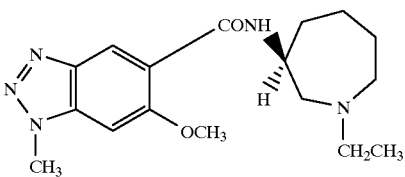

Compound of Example 8b (Compound 8b)
(S)-N-(1-ethyl-1H-hexahydroazepin-3-yl)-6-methoxy-1H-benzotriazole-5-carboxamide.3/2 fumarate

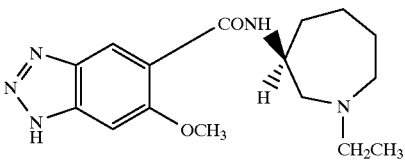

Compound A
4-Amino-5-chloro-N-[2-(diethylamino)ethyl]-2-methoxybenzamide hydrochloride monohydrate [generic name: metoclopramide; see, for example, *Merck Index*, 11th ed. 6063 (1989)]

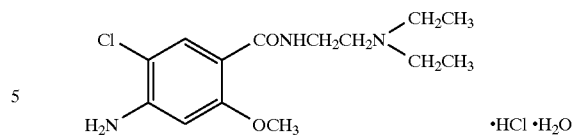

Experiment 1

Inhibitory effect on apomorphine-induced vomiting

A group of 3–4 dogs (Beagle, 8–15 kg) was used for examining inhibitory effects of the test compounds on apomorphine-induced vomiting according to the method of Chen and Ensor [cf. *J. Pharmacol. Exp. Ther.*, 98, 245–250 (1950)]. Test compounds, dissolved or suspended in a 0.5% tragacanth solution were orally administered two hours before the subcutaneous administration of apomorphine hydrochloride (0.3 mg/kg). Then, the emetic episodes were counted for one hour. The emetic episodes of the compound-treated group were compared with those of the corresponding control (non-dosed) group, and the percent inhibition was calculated. The results are shown in Table 1.

TABLE 1

Inhibitory effect on apomorphin-induced vomiting

| Test comp. | Dose (mg/kg) | Inhibition (%) | Test comp. | Dose (mg/kg) | Inhibition (%) |
|---|---|---|---|---|---|
| 1 | 1.0 | 77 | 9 | 1.0 | 100 |
| 2 | 1.0 | 100 | 10 | 1.0 | 100 |
|   | 0.1 | 80 | 11 | 1.0 | 92 |
| 4 | 1.0 | 89 | 12 | 1.0 | 92 |
| 5 | 1.0 | 100 | 13 | 1.0 | 73 |
| 6 | 1.0 | 100 | 14 | 1.0 | 100 |
|   | 0.3 | 71 | 15 | 1.0 | 71 |
| 7a | 1.0 | 100 | 3 | 1.0 | 36 |
|   | 0.1 | 73 | 8b | 1.0 | 19 |
| 7b | 1.0 | 100 | Compound | 1.0 | 86 |
|   | 0.1 | 69 | A | 0.5 | 56 |

As is clear from Table 1, almost all of the tested compounds of the present invention showed an activity equal to or more potent than metoclopramide hydrochloride monohydrate (Compound A) in inhibiting apomorphine-induced vomiting.

Experiment 2

Gastric emptying enhancing activity

The test was carried out according to the method of Scarpignato et al. [cf. *Arch. Int. Pharmacodyn.*, 246, 286–294 (1980)]. Male Wistar rats, weighing 130–150 g, were fasted for 18 hours before experimentation, and 1.5 ml of a test meal (phenol red 0.05% in a 1.5% aqueous methylcellulose solution) was orally given. Fifteen minutes after administration of the meal the stomach was removed and the amount of phenol red remaining in the stomach was measured. The test compounds, dissolved or suspended in a 0.5% tragacanth solution, were orally administered 60 minutes before administration of the test meal. The rate of gastric emptying was calculated according to the amount of phenol red remaining in the stomach, and the activity of the test compounds was expressed in terms of increase in the emptying rate from the control. The number of animals used was 4 for the tested compounds of the present invention and 5 for the Compound A used for comparison. The results are shown in Table 2.

TABLE 2

Gastric emptying enhancing activity

| Test compound | Dose (mg/kg) | Increase (%) |
|---|---|---|
| 2 | 3 | 41 |
| 4 | 3 | 31 |
| 5 | 3 | 35 |
| 6 | 3 | 28 |
| 7b | 3 | 34 |
| 10 | 3 | 46 |
| 11 | 3 | 34 |
| 14 | 3 | 32 |
| Compound A | 10 | 31 |
|  | 5 | 26 |
|  | 2 | 21 |

As is clear from Table 2, each tested compound of the present invention showed an activity equal to or more potent than metoclopramide hydrochloride monohydrate (Compound A) in enhancing gastric emptying.

Experiment 3
Effect on gastric emptying delayed by cholecystokinin or morphine

The test was carried out according to the method of Scarpignato et al. [c f. Arch. int. Pharmacodyn., 246, 286–294 (1980)]. Male Wistar rats, weighing 130–150 g, were fasted for 18 hours before experimentation, and 1.5 ml of a test meal (phenol red 0.05% in a 1.5% aqueous methylcellulose solution) was orally given. Fifteen minutes after administration of the meal the stomach was removed and the amount of phenol red remaining in the stomach was measured.

The test compounds, 10, 30 or 100 mg/kg, each dissolved or suspended in a 0.5% tragacanth solution, were orally administrated 60 minutes before administration of the test meal. Gastric emptying was delayed by subcutaneous administration of cholesystokinin 3 µg/kg or morphine 3 mg/kg 5 minutes before the administration of phenol red. The number of animals used was 5 to 10. The results are shown in Table 3.

TABLE 3

Effect on gastric emptying delayed by cholecystokinin or morphine

| Test compound | Dose (mg/kg) | Cholecystokinin | Morphine |
|---|---|---|---|
| 2 | 30 | + |  |
|  | 100 | ++ |  |
| 7b | 10 | + | + |
|  | 30 | ++ | ++ |
|  | 100 | ++ | ++ |
| Compound A | 10 | ± | ± |
|  | 30 | ± | ± |
|  | 100 | ± | ± |

+: slightly to moderately improved
++: markedly improved
±: no improvement

Test compound 2 (Compound of Example 2) of the present invention at the doses of 30 or 100 mg/kg significantly improved gastric emptying delayed by cholecystokinin. Test compound 7b (Compound of Example 7b) of the present invention at the doses of 10, 30 or 100 mg/kg significantly improved gastric emptying delayed by cholecystokinin or morphine, and showed excellent gastrointestinal motility enhancing activity (gastroprokinetic activity) against gastric emptying delayed by cholecystokinin or morphine at each dose. On the other hand, metoclopramide hydrochloride monohydrate (Compound A) at the doses of 10, 30 or 100 mg/kg did not show an improving activity against the delay in gastric emptying induced by cholecystokinin or morphine.

Experiment 4
Effect on gastrointestinal motility in conscious dog

Four healthy beagle dogs per group of both sexes weighing 10 to 12 kg were anesthetized with an i.v. injection of pentobarbital sodium (Nembutal, 30 mg/kg b. wt.), and the abdominal cavity was opened under aseptic conditions.

Extraluminal force transducers were sutured onto the seromuscular layer of the gastric antrum, 3 cm proximal to the pyloric ring, the duodenum, the jejunum, the midintestine and the terminal ileum in a manner to measure circular muscle contraction, following the method of Ito et al., [cf. Gastrointerol. Japan. 12, 275–283 (1977).] For intragastric (i.g.) administration of drugs, a Silastic tube (Fr. size 6.5) was inserted into the lumen of the gastric body, and the tube was fixed onto the adjacent serosa. The lead wires of these transducers and gastric tube were taken out of abdominal cavity and then brought out through a skin incision made between the scapulae. The outer ends of the lead wires were sutured onto the skin adjacent to the skin incision. After the operation, jacket protector was placed on the dog to protect the lead wires and the Silastic tube. The dogs were housed in individual experimental cages and given dog food at 10 a.m., and water was given freely.

Test compounds at 3 and 10 mg/kg were suspended in 0.5% tragacanth solution and given i.g. through the indwelling Silastic tube.

Compounds 2 and 7b of the present invention at doses of 3 and 10 mg/kg caused interdigestive migrating like-contractions in fed state in conscious dogs. Thus, it was found that test compounds showed remarkable gastrointestinal motility enhancing activity (gastroprokinetic activity). In contrast, Compound A did not cause interdigestive migrating contractions at all.

Experiment 5
Inhibitory effect on exploratory activity

A group of 5 male mice (Std-ddy strain, 20–25 g) was used. Two hours after oral administration of the test compounds in the form of 0.5% tragacanth solution or suspension, mice were placed individually in a test box (23×35×30 cm) on Animex activity meter (Farad Co.). Immediately thereafter, activity counting was started and lasted for three minutes. The mean counts of the compound-treated group were compared with those of the corresponding control (non-dosed) group, and the percent inhibition was calculated and the 50% inhibitory dose ($ID_{50}$) was obtained according to the method of Probit. The results are shown in Table 4.

TABLE 4

Inhibitory effect on exploratory activity

| Test Compound | $ID_{50}$ (mg/kg) |
|---|---|
| 1 | >100 |
| 2 | >100 |
| 4 | >100 |
| 6 | >100 |
| 7a | >100 |
| 7b | >100 |
| Compound A | 22.4 |

As is clear from Table 4, each tested compound of the present invention showed far less inhibitory effect on exploratory activity than metociopramide hydrochloride monohydrate (Compound A). This result suggests that these compounds of the present invention showed far less central nervous depression compared with that of Compound A.

Experiment 6

Acute toxicity

A group of 5 male mice (Std-ddy strain, 25–30 g) was used. The test compound was orally administered to the test animal in the form of a 0.5% tragacanth solution or suspension, and for 7 days after the administration of the test compounds, lethality of animals was observed, and the 50% lethal dose ($LD_{50}$) was determined. The results are shown in Table 5.

TABLE 5

Acute toxicity

| Test Compound | $LD_{50}$ (mg/kg) |
| --- | --- |
| 2 | 688 |
| 7b | 945 |
| Compound A | 280 |

As can be seen from the test results given above, the compounds of formula (I) of the present invention and their pharmaceutically acceptable acid addition salts have both of excellent inhibitory effect on vomiting and gastrointestinal motility enhancing activity (gastroprokinetic activity) with less CNS depressant activity and less toxicity, and hence, are useful as gastrointestinal motility improving agent (gastroprokinetic agent) for the treatment and prophylaxis of various gastrointestinal function disorders associated with various diseases and treatments; for example, anorexia, nausea, vomiting, abdominal fullness, upper abdominal discomfort, abdominal pain, heartburn and eructation (belching) which are seen in acute and chronic gastritis, esopaphageal reflux, gastric and duodenal ulcer, gastric neurosis, gas troptosis, paralyticus ileus after surgery, senile ileus, postgastrectomy syndrome, scleroderma, diabetes, esophageal and biliary duct disorders, puerile periodic vomiting, upper respiratory tract infections; for example, irritable bowel syndrome, constipation, infant diarrhea; and for example, nausea and vomiting following administration of anticancer agents or levodopa preparations, or following X-ray irradiation.

Of the compounds of the present invention, Compounds 2, 7a and 7b show especially excellent gastrointestinal motility improving activity.

The pharmaceutical preparations can be administered by oral, parenteral or intrarectal route. The clinical dose varies depending on the kinds of the compounds, administration routes, severity of disease, age of patients, or the like, but is usually in the range of 0.01 to 10 mg/kg/day, preferably 0.1 to 3 mg/kg/day.

For using the compounds of formula (I) or their pharmaceutically acceptable acid addition salts for such medicinal use as above, they are normally administered to the patients in the form of pharmaceutical preparations formulated by mixing with carriers which are conventionally used in the field of medical formulations and which do not react with the compounds of the present invention. More specifically, for example, such carriers as lactose, inositol, glucose, mannitol, dextran, sorbitol, cyclodextrin, starch, partly pregelatinized starch, sucrose, magnesium aluminometasilicate, synthetic aluminum silicate, microcrystalline cellulose, sodium carboxymethylcellulose, hydroxypropylstarch, calcium carboxymethylcellulose, ion exchange resin, methylcellulose, gelatin, acacia, pullulan, hydroxypropylcellulose, low substituted hydroxypropylcellulose, hydroxypropyl methylcellulose, polyvinylpyrrolidone, polyvinylalcohol, alginic acid, sodium alginate, light anhydrous silicic acid, magnesium stearate, talc, tragacanth, bentonite, veegum, carboxyvinyl polymer, titanium dioxide, sorbitan fatty acid ester, sodium lauryl sulfate, glycerin, glycerides of saturated fatty acids, anhydrous lanolin, glycerogelatin, polysorbate, macrogol, vegetable oils, wax, water, propylene glycol, ethanol, sodium chloride, sodium hydroxide, hydrochloric acid, citric acid, benzyl alcohol, glutamic acid, glycine, methyl parahydroxybenzoate, propyl parahydroxybenzoate and the like may be named.

The pharmaceutical compositions may take any of such preparation forms as tablets, capsules, granules, powders, syrups, suspensions, injections, cataplasms, suppositories, and the like, which are prepared by conventional methods. Liquid preparations may take such forms which are dissolved or suspended in water or other suitable media before use. The tablets and granules may be coated by the methods well known per se.

The compounds of the present invention as represented by the formula (I) in which $R^2$ is hydrogen display good solubility in water and hence are particularly convenient for liquid preparations.

These preparations can contain at least 0.01% of a compound of formula (I) of the present invention or a pharmaceutically acceptable acid addition salt thereof, preferably at a proportion between 0.1 and 70%. The preparations may also contain other therapeutically valuable component(s).

BEST MODE FOR CARRYING OUT THE INVENTION

Hereinafter the present invention is explained more specifically, referring to the referential examples and working examples, it being understood that the invention is in no way limited thereby. The identification of the formed compounds was carried out based on such data as elemental analysis, mass spectrum, UV spectrum, IR spectrum, NMR spectrum and the like.

In the following referential and working examples, the following abbreviations are occasionally used for simplifying the description.

Recrystallization solvent

A: ethanol

E: diethyl ether

Substitutent

Me: methyl

Et: ethyl

Δ: cyclopropyl

Ph: phenyl

NMR

J: coupling constant s: singlet d: doublet dd: double doublet t: triplet q: quartet m: multiplet br-s: broad singlet Others ee: enantiomeric excess

EXAMPLE 1 a reaction by process (b)

Preparation of N-(1-ethyl-1H-hexahydroazepin-3-yl)-6-methoxy-1-methyl-1H-benzotriazole-5-carboxamide (Compound 1)

To 40 ml of an aqueous solution containing about 3.0 g of 5-amino-N-(1-ethyl-1H-hexahydroazepin-3-yl)-2-methoxy-4-methylaminobenzamide which had been obtained in the later-appearing Referential Example 4, 5 ml of acetic acid was added. The solution was then cooled to 5° C., to which 10 ml of an aqueous solution containing 0.8 g of sodium nitrite was added, following by an hour's stirring at the same temperature. The reaction mixture was basified with aqueous sodium hydroxide, and extracted with chloroform. The extract was washed with water, dried over anhydrous magnesium sulfate, and the solvent was evaporated under reduced pressure to give an oily residue. The oil was subjected to silica gel column chromatography, whereby eluted and purified with chloroform-methanol (9:1). The resulting solid was recrystallized from toluene-n-hexane to provide 2.3 g of the title compound, m.p. 103–104° C.

EXAMPLE 2 a reaction by process (b)

Preparation of (R)-N-(1-ethyl-1H-hexahydroazepin-3-yl)-6-methoxy-1-methyl-1H-benzotriazole-5-carboxamide (Compound 2)

An aqueous acetic acid solution containing (R)-5-amino-N-(1-ethyl-1H-hexahydroazepin-3-yl)-2-methoxy-4-methylaminobenzamide which had been obtained in the later appearing Referential Example 5 was cooled to 5° C., into which 50 ml of an aqueous solution containing 6.6 g of sodium nitrite was added dropwise. The mixture was stirred for an hour at the same temperature, and then for two hours at room temperature. The reaction mixture was basified with aqueous sodium hydroxide solution and extracted with ethyl acetate. The extract was washed with water, dried over anhydrous magnesium sulfate, and the solvent was evaporated under reduced pressure to give an oily residue. The oil was subjected to silica gel column chromatography, and whereby eluted and purified with chloroform-methanol (9:1). The resulting solid was recrystallized from toluene-n-hexane to provide 26.7 g of the title compound, m.p. 118–120° C.

$[\alpha]_D^{27}$–70.6° (c=1,0, ethanol).

EXAMPLE 3 a reaction by process (b)

Preparation of (S)-N-(1-ethyl-1H-hexahydroazepin-3-yl)-6-methoxy-1-methyl-1H-benzotriazole-5-carboxamide (Compound 3)

The reaction and treating were conducted in the manner similar to Example 2, using an aqueous solution of (S)-5-amino-N-(1-ethyl-1H-hexahydroazepin-3-yl)-2-methoxy-4-methylaminobenzamide which had been obtained in the later appearing Referential Example 6. The product obtained was recrystallized from toluene-n-hexane to produce the title compound, m.p. 119–120° C.

EXAMPLE 4 a reaction by process (b)

Preparation of 1-ethyl-N-(1-ethyl-1H-hexahydroazepin-3-yl)-6-methoxy-1H-benzotriazole-5-carboxamide (Compound 4)

The reaction and treating were carried out in the manner similar to Example 1, using an aqueous solution of 5-amino-N-(1-ethyl-1H-hexahydroazepin-3-yl)-4-ethylamino-2-methoxybenzamide which had been obtained in the later-appearing Referential Example 7. The product obtained was recrystallized from toluene-n-hexane to produce the title compound, m.p. 84–85° C.

EXAMPLE 5 a reaction by process (b)

Preparation of (R)-1-ethyl-N-(1-ethyl-1H-hexahydroazepin-3-yl)-6-methoxy-1H-benzotriazole-5-carboxamide (Compound 5)

The reaction and treating were carried out in the manner similar to Example 1, using an aqueous solution of (R)-5-amino-N-(1-ethyl-1H-hexahydroazepin-3-yl)-4-ethylamino-2-methoxybenzamide which had been obtained in the later-appearing Referential Example 8. The product was obtained as an oil: mass spectrum (m/z): 346 (MH$^+$).

EXAMPLE 6 a reaction by process (a)

Preparation of N-(1-ethyl-1H-hexahydroazepin-3-yl)-6-methoxy-1H-benzotriazole-5-carboxamide (Compound 6)

To 10 ml of a dimethylformamide solution containing 0.85 g of 6-methoxy-1H-benzotriazole-5-carboxylic acid, 0.78 g of N,N'-carbonyldiimidazole was added and stirred for 6 hours at room temperature. 0.75 Gram of 3-amino-1-ethyl-1H-hexahydroazepine was added to the reaction mixture, followed by 14 hours' stirring at room temperature. After the reaction terminated, the solvent was evaporated under reduced pressure, and the residue was subjected to a silica gel column chromatography, whereby eluted and purified with chloroform-methanol (10:1). The product obtained was recrystallized from ethanol-diethyl ether to provide 1.3 g of the title compound, m.p. 156–158° C.

$^1$H-NMR spectrum (CDCl$_3$, δ (ppm): 1.09 (3H, t, J=7 Hz), 1.5–2.1 (6H, m), 2.5–3.1 (6H, m), 3.83 (3H, s), 4.4(1H, m), 6.4 (1H, br-s), 7.07 (1H, s), 8.05 (1H, d, J=8 Hz), 8.78 (1H, s).

EXAMPLE 7 a reaction by process (a) and a reaction by process (d)

Preparation of (R)-N-(1-ethyl-1H-hexahydroazepin-3-yl)-6-methoxy-1H-benzotriazole-5-carboxamide (Compound 7a)

(a) a reaction by process (a)

To 150 ml of a dimethylformamide solution containing 10 g of 6-methoxy-1H-benzotriazole-5-carboxylic acid, 9.0 g of N,N'-carbonyldiimidazole was added and stirred for 6 hours at room temperature. To the reaction mixture 8.8 g of (R)-3-amino-1-ethyl-1H-hexahydroazepine was added and stirred for 14 hours at room temperature. After the reaction terminated, the solvent was evaporated under reduced pressure, and the residue was subjected to a silica gel column chromatography, whereby eluted and purified with chloroform-methanol (10:1). The product obtained was recrystallized from diethyl ether-n-hexane to provide 12 g of the title compound (Compound 7a), m.p. 127–128° C.

(a') The title compound was once again recrystallized from ethyl acetate-n-hexane to give the title compound, m.p. 142–144° C.

$[\alpha]_D^{25}$–71.9° (c=1,0, methanol).

This compound showed a retention time of 37.2 minutes in the high performance liquid chromatography (HPLC) under the following conditions, and had an optical purity of 99% ee or higher.

HPLC conditions

HPLC column: SUMICHIRAL OA-4900; 4.6 mm×250 mm, manufactured by Sumitomo Chemical Analysis Center Mobile phase: n-hexane-methylene chloride-ethanol-trifluoroacetic acid (400:100:100:0.6)

Flow rate: 1.0 ml/min.
Temp.: 25° C.
Detection: 230 nm.

From the starting material having R-configuration, the above title compound having an optical purity of 99% ee or higher was obtained by means of the high performance liquid chromatography, not accompanied by racemization. Furthermore, in the later appearing Example 8, a compound of S-configuration having an optical purity of 99% ee or higher was obtained from a starting material of S-configuration without racemization. These facts clearly indicate that the configuration of the title compound obtained in this Example is R.

(b) The product as obtained in above (a) was treated with fumaric acid to be converted to the corresponding fumarate, which was recrystallized form isopropyl alcohol-methanol to provide 3/2 fumarate of the title compound (Compound 7b), m.p. 131–133° C.

(b') The product as obtained in above (a) was treated with fumaric acid to be converted to the corresponding fumarate, which was recrystallized from isopropyl alcohol to provide 3/2 fumarate of the title compound, m.p. 162–163° C.

(b") The product as obtained in above (a) was treated with fumaric acid and converted to the correponding fumarate, which was recrystallized from ethanol-isopropyl alcohol to provide 3/2 fumarate.1/4 hydrate of the title compound, m.p. 166–168° C.

(c) The reaction using the compound of formula (III) in which $R^2$ is acetyl group (amino-protective group)
a reaction by process (a)

To 31.5 g of 1-acetyl-6-methoxy-1H-benzotriazole-5-carboxylic acids 20.3 g of triethylamine and 400 ml of ethyl acetate were added, and to the mixture 17.5 g of ethyl chloroformate was added dropwise at −7 to −10° C. After the following 2 hours' stirring at −5° C. to −7° C., 80 ml of an ethyl acetate solution containing 22.8 g of (R)-3-amino-1-ethyl-1H-hexahydroazepine was added dropwise to the mixture which was stirred for an hour at the same temperature and then for 16 hours at room temperature. The reaction mixture was washed with water and saturated aqueous sodium chloride solution, and dried over anhydrous sodium sulfate, and the solvent was evaporated under reduced pressure. The residue was resolved in 1000 ml of a chloroform-methanol (8:1) mixture, and then 180 g of silica gel was added to the solution, followed by 16 hours' stirring at room temperature. The silica gel was removed by filtration, and the residue was washed with 1000 ml of a chloroform-methanol (5:1) mixture. The solvent was evaporated under reduced pressure to give 32 g of the crude object product.

Twenty-four (24) g of above crude product was treated with 2.5–3 times by volume (22.5 g) of fumaric acid, and the formed fumarate was recrystallized from methanol-isopropyl alcohol to provide 25 g of 3/2 fumarate of the title compound, m.p. 131–133° C.

(d) a reaction by process (d)

To 1.85 g of (R)-1-acetyl-N-(1-ethyl-1H-hexahydroazepin-3-yl)-6-methoxy-1H-benzotriazole-5-carboxamide which was obtained in later appearing Example 17, 55 ml of a chloroform-methanol (8:1) mixture was added. Further 18.5 g of silica gel was added, and the mixture was stirred for 16 hours at room temperature. The silica gel was removed by filtration, and the residue was washed with a chloroform-methanol (9:1) mixture containing 1% aqueous ammonia. The solvent was evaporated under reduced pressure to give 1.78 g of the crude object product.

EXAMPLE 8 a reaction by process (a)
Preparation of (S)-N-(1-ethyl-1H-hexahydroazepin-3-yl)-6-methoxy-1H-benzotriazole-5-carboxamide (Compound 8)

(a) (R)-3-amino-1-ethyl-1H-hexahydroazepine in Example 7 was replaced by (S)-3-amino-1-ethyl-1H-hexahydroazepine which was treated and worked up in the manner similar to Example 7 to provide the title compound.

(b) The above product was treated with fumaric acid and converted to the corresponding fumarate. Recrystallization from isopropyl alcohol gave a 3/2 fumarate of the title compound, m.p. 156–158° C.

The title compound showed a retention time of 44.0 minutes in HPLC under the same conditions with those specified in Example 7, and had an optical purity of 99% ee or higher.

(b') The above product of (a) was treated with fumaric acid similarly to (b) above, and the formed fumarate was recrystallized from ethanol-isopropyl alcohol. A difumarate.1/2 hydrate of the title compound was obtained, m.p. 148–151° C.

EXAMPLES 9–12 a reaction by process (a)
Example 6 was repeated except that the 3-amino-1-ethyl-1H-hexahydroazepine was replaced by the corresponding 3-amino-1-substituted-1H-hexahydroazepines. Thus those compounds as presented in Table 6 were obtained.

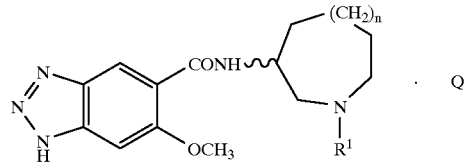

TABLE 6

| Example | configuration | $R^1$ | n | Q | mp. (° C.) | recrystallization solvent |
|---|---|---|---|---|---|---|
| 9 | RS | Et | 2 | 1/4H$_2$O | 169–171 | E |
| 10 | RS | Et | 3 | | 200–202 | A–E |
| 11 | RS | CH$_2$—◁ | 1 | | amorphous | |
| 12 | R | CH$_2$—◁ | 1 | | amorphous | |

EXAMPLE 13 a reaction by process (b)
Preparation of (R)-N-(1-cyclopropylmethyl-1H-hexahydroazepin-3-yl)-6-methoxy-1-methyl-1H-benzotriazole-5-carboxamide (Compound 13)

Using the corresponding starting compound, an aqueous solution of (R)-5-amino-N-(1-cyclolpropylmethyl-1H-hexahydroazepin-3-yl)-2-methoxy-4-methylaminobenzamide was obtained through the reaction and treating in the manner similar to those of later-appearing Example 19 and Referential Examples 1 and 4. This solution was treated and worked up in the manner similar to Example 1, and the resultant product was recrystallized from toluene to provide the title compound, m.p. 127–128° C.

EXAMPLE 14
a reaction by process (a)
Preparation of N-(1-ethyl-1H-heptahydroazocin-3-yl)-6-methoxy-1-methyl-1H-benzotriazole-5-carboxamide (Compound 14)

Example 6 was repeated except that the 6-methoxy-1H-benzotriazole-5-carboxylic acid and 3-amino-1-ethyl-1H-hexahydroazepine used in Example 6 were replaced by 6-methoxy-1-methyl-1H-benzotriazole-5-carboxylic acid and 3-amino-1-ethyl-1H-heptahydroazocine, respectively. The resulting product was recrystallized from ethanol-diethyl ether to provide the title compound, m.p. 116–118° C.

EXAMPLE 15
a reaction by process (a)
Preparation of N-(1-ethyl-1H-octahydroazonin-3-yl)-6-methoxy-1-methyl-1H-benzotriazole-5-carboxamide (Compound 15)

Example 6 was repeated except that the 6-methoxy-1H-benzotriazole-5-carboxylic acid and 3-amino-1-ethyl-1H-hexahydroazepine used in Example 6 were replaced by 6-methoxy-1-methyl-1H-benzotriazole-5-carboxylic acid and 3-amino-1-ethyl-1H-octahydroazonine, respectively. The resulting product was recrystallized from ethyl acetate to provide the title compound, m.p. 155–156° C.

In the following Examples 16–24, synthetic methods of the intermediates which are useful for preparing the compounds of the present invention are described.

EXAMPLE 16
a reaction by process (b)
Preparation of 1-benzyl-N-(1-ethyl-1H-hexahydroazepin-3-yl)-6-methoxy-1H-benzotriazole-5-carboxamide [a compound of formula (IIa) in which $R^{3a}$ is benzyl group]

To 6 ml of an aqueous hydrochloric acid solution containing about 1.5 g of 5-amino-4-benzylamino-N-(1-ethyl-1H-hexahydroazepin-3-yl)-2-methoxybenzamide which was obtained in later-appearing Referential Example 9, 30 ml of 5N hydrochloric acid and 70 ml of water were added. To the solution then 1 ml of an aqueous solution containing 0.29 g of sodium nitrite was added under ice-cooling, followed by 30 minutes' stirring under the same condition and an hour's stirring at room temperature. The reaction mixture was basified with 48% aqueous sodium hydroxide solution, and extracted with chloroform. The extract was washed with saturated aqueous sodium chloride solution, dried over anhydrous magnesium sulfate, and the solvent was evaporated under reduced pressure to provide an oily residue. The residue was subjected to silica gel column chromatography wherein it was eluted and purified with chloroform-methanol (20:1). The resultant solid was recrystalized from diethyl ether to provide 1.1 g of the title compound, m.p. 136–137° C.

EXAMPLE 17
a reaction by process (a)
Preparation of (R)-1-acetyl-N-(1-ethyl-1H-hexahydroazepin-3-yl)-6-methoxy-1H-benzotriazole-5-carboxamide [a compound of formula (IIb) in which $R^{3b}$ is acetyl group]

To 31.5 g of 1-acetyl-6-methoxy-1H-benzotriazole-5-carboxylic acid, 20.3 g of triethylamine and 400 ml of ethyl acetate were added. To the solution then 17.5 g of ethyl chloroformate was added dropwise at −7 to −10° C., followed by two hours' stirring at −5° C. to −7° C. Eighty (80) ml of ethyl acetate solution containing 22.8 g of (R)-3-amino-1-ethyl-1H-hexahydroazepine was added dropwise to the mixture which was subsequently stirred for an hour, and then for 16 hours at room temperature. The reaction mixture was washed successively with water, and then with saturated aqueous sodium chloride solution and dried over anhydrous sodium sulfate. The solvent was evaporated under reduced pressure, 36 g of the title compound was obtained as a solid. m.p. 134–135° C. (recrystallized from ethyl acetate)

$^1$H-NMR spectrum (CDCl$_3$, δ ppm): 1.04 (3H, t, J=7.0 Hz), 1.5–2.1 (6H, m), 2.45–2.95 (6H, m), 3.00 (3H, s), 4.09 (3H, s), 4.35 (1H, br-s), 7.76 (1H, s), 8.60 (1H, d, J=9.0 Hz), 8.95 (1H, s).

EXAMPLE 18
a reaction according to scheme 1
Preparation of (R)-3-amino-1-ethyl-1H-hexahydroazepine (1) Step 1:

To a stirred suspension of 173 g of (R)-α-amino-ε-caprolactam hydrochloride, 266 g of triethylamine and 1,700 ml of chloroform, 293 g of chlorotriphenylmethane was added portionwise under ice-cooling. The resulting mixture was stirred for an hour under the same conditions, and then for two hours at room temperature. The reaction mixture was washed with water and dried over anhydrous magnesium sulfate. The solvent was evaporated under reduced pressure, and to the resultant oily residue 600 ml of n-hexane-ethyl acetate (2:1) mixture was added under heating and stirring. The crystalline precipitates obtained were collected by filtration, washed with 1,000 ml of n-hexane-ethyl acetate (10:1) mixture and dried to provide 290 g of (R)-α-triphenylmethylamino-ε-caprolactam, m.p. 189° C.

(2) Step 2':

To a mixture of 300 g of the above product, 193 g of ethane iodide and 1,500 ml of tetrahydrofuran, 42 g of 60% sodium hydride was gradually added under stirring at room temperature, followed by 1.5 hours' stirring under the same conditions. Then the vessel was cooled with ice water, and water was slowly added to the mixture until the insoluble materials were dissolved. The reaction mixture was concentrated under reduced pressure, and to the residue 1,000 ml of ethyl acetate was added. Washing the solution with water, the organic layer was dried over anhydrous magnesium sulfate, and the solvent was evaporated under reduced pressure. To the resultant oily residue 350 ml of a hexane-ethyl acetate (50:1) mixture was added, and resulting crystalline precipitates were collected by filtration, and dried to give 287 g of (R)-1-ethyl-3-triphenylmethylamino-1H-hexahydroazepin-2-on, m.p. 127° C.

(3) Step 3':

To 615 g of a 70% toluene solution of sodium bis(2-methoxyethoxy)aluminum hydride, 1400 ml of toluene was added, and to the mixture 280 g of above product was added with stirring and ice-cooling. The solution was stirred for 1.5 hours under the same conditions. To the resulting reaction mixture, 1,000 ml of 15% aqueous sodium hydroxide solution was added under ice-cooling, and the organic layer was separated, and then the aqueous layer was extracted with 1,500 ml of toluene. The combined organic layer was washed with water, and dried over anhydrous magnesium sulfate, and the solvent was evaporated under reduced pressure. Thus obtained oily residue was crystallized from ethanol. The resulting crystallines were collected by filtration and dried to give 247 g of (R)-1-ethyl-3-triphenylmethylamino-1H-hexahydroazepine, m.p. 83–84° C.

(4) Step 4:

To a mixture of 177 g of the above product and 50 ml of tetrahydrofuran, 700 ml of 10% hydrochloric acid was added, followed by 2 hours' stirring at room temperature. The reaction mixture was washed with diethyl ether. Then an excess amount of potassium carbonate was added to the aqueous layer, followed by extraction with chloroform. The liquid extract was dried over anhydrous magnesium sulfate and the solvent was evaporated under reduced pressure. Thus 65 g of the title compound was obtained as an oil.

$^1$H-NMR spectrum (CDCl$_3$, δ ppm): 1.04 (3H, t, J=7.5 Hz), 1.3–1.9 (8H, m), 2.42 (1H, dd, J=13.5 Hz, 6.9 Hz), 2.5–2.6 (4H, m), 2.70 (1H, dd, J=13.5, J=3.5 Hz), 2.98 (1H, m).

EXAMPLE 19
a reaction according to scheme 1
Preparation of (R)-3-amino-1-cyclopropylmethyl-1H-hexahydroazepine (1) Step 2:

To a mixture of 370 ml of toluene and 37 g of (R)-α-triphenylmethylamino-ε-caprolactam, 1,000 ml of 1M toluene solution of diisobutylaluminum hydride was added dropwise at room temperature, followed by 16 hours' stirring. After termination of the reaction, water was added dropwise to the mixture to decompose the excessive diisobutylaluminum hydride. The precipitated salts were removed by filtration, and the filtrate was washed with saturated aqueous sodium chloride solution, and dried over anhydrous magnesium sulfate, and the solvent was evaporated under reduced pressure. Thus 34 g of (R)-3-triphenylmethylamino-1H-hexahydroazepine was obtained as an oil.

(2) Step 3:

To a mixture of 10 g of the above product and 100 ml of methyl ethyl ketone, 10.5 g of potassium carbonate and 5.1 g of cyclopropylmethyl bromide were added, and the mixture was heated for 5 hours under reflux. After termination of the reaction, the insoluble materials were removed by filtration, and the filtrate was concentrated under reduced pressure. The residue was subjected to silica gel column chromatography, whereby eluted and purified with chloroform-methanol (10:1) to provide 10 g of (R)-1-cyclopropylmethyl-3-triphenylmethylamino-1H-hexahydroazepine as an oil.

(3) Step 4:

To a mixture of 9.0 g of the above product and 10 ml of tetrahydrofuran, 100 ml of 10% hydrochloric acid was added, followed by stirring for 5 hours at room temperature. The resulting reaction mixture was washed with diethyl ether, and the aqueous layer was saturated with potassium carbonate and extracted with chloroform. The extract was dried over anhydrous magnesium sulfate and the solvent was evaporated under reduced pressure, to provide 4.0 g of the title compound as an oil.

EXAMPLE 20
a reaction according to scheme 1
Preparation of 3-amino-1-ethyl-1H-hexahydroazepine (1) Step 1:

To a stirred suspension of 125 g of α-amino-ε-caprolactam, 118 g of triethylamine and 600 ml of chloroform, 288 g of chlorotriphenylmethane was added under ice-cooling. The mixture was further stirred for an hour under the same conditions, followed by 2 hours' stirring at room temperature. Thus resulting precipitates were collected by filtration, washed thoroughly with acetone and dried to provide 330 g of α-triphenylmethylamino-ε-caprolactam, m.p. 240–241° C.

(2) Step 2':

To a solution of 100 g of the above product and 65 g of ethane iodide in 500 ml of dimethylformamide, 12 g of 60% sodium hydride was gradually added under stirring at room temperature, followed by 4 hours' stirring under the same conditions. The whole was then poured into ice water, and was extracted with diethyl ether. The extract was washed with water, and dried over anhydrous magnesium sulfate, and the solvent was evaporated under reduced pressure. The resulting crystallines were collected by filtration and dried to provide 88 g of 1-ethyl-3-triphenylmethylamino-1H-hexahydroazepin-2-on, m.p. 120–121° C.

(3) Step 3':

To 180 g of 70% toluene solution containing sodium bis(2-methoxyethoxy)aluminum hydride, 800 ml of toluene was added. Further 83 g of the above product was added under stirring and ice-cooling, followed by an hour's stirring under the same conditions and 2 hours' stirring at room temperature. To the reaction mixture, water and 48% aqueous sodium hydroxide solution were added under ice-cooling, and the organic layer was separated. The organic layer was washed with water, and dried over anhydrous magnesium sulfate, and the solvent was evaporated under reduced pressure. Thus obtained oily residue was crystallized from ethanol. The crystallines were collected by filtration and dried to give 65 g of 1-ethyl-3-triphenylmethylamino-1H-hexahydroazepine, m.p. 85–86° C.

(4) Step 4:

To a mixture of 134 g of the above product and 30 ml of tetrahydrofuran, 500 ml of 10% hydrochloric acid was added, followed by 2 hours' stirring at room temperature. The reaction mixture was washed with diethyl ether. Then an excess potassium carbonate was added to the aqueous layer and extracted with chloroform. The extract was dried over anhydrous magnesium sulfate and the solvent was evaporated under reduced pressure, to provide 48 g of the title compound as an oil.

$^1$H-NMR spectrum (CDCl$_3$, δ ppm): 1.04 (3H, t, J=7.5 Hz), 1.3–1.9 (8H, m), 2.42 (1H, dd, J=13.5 Hz, 6.9 Hz), 2.5–2.6 (4H, m), 2.70 (1H, dd, J=13.5, J=3.5 Hz), 2.98 (1H, m).

EXAMPLE 21
a reaction according to scheme 1
Preparation of (S)-3-amino-1-ethyl-1H-hexahydroazepine Example 20 was repeated except that α-amino-ε-caprolactam used in the step 1 therein was replaced by (S)-α-amino-ε-caprolactam. The title compound was obtained as an oil.

EXAMPLE 22
a reaction according to scheme 1
Preparation of 3-amino-1-cyclopropylmethyl-1H-hexahydroazepine Example 18 was repeated except that (R)-α-triphenylmethylamino-ε-caprolactam used in the step 1 therein was replaced by α-triphenylmethylamino-ε-caprolactam. The title compound was obtained as an oil.

EXAMPLE 23
a reaction according to scheme 2
Preparation of 3-amino-1-ethyl-1H-heptahydroazocine (1) Step 1:

To a solution of 27 g of 2-azacyclooctanone and 50 g of ethane iodide in 250 ml of tetrahydrofuran, 10 g of 60% sodium hydride was gradually added under stirring and ice-cooling. The reaction mixture was stirred for 4 hours at room temperature and poured into ice water, followed by extraction with diethyl ether. The extract was dried over anhydrous magnesium sulfate and the solvent were evaporated under reduced pressure. The residue was subjected to silica gel column chromatography, whereby eluted and purified with chloroform-methanol (100:1) to give 36 g of 1-ethyl-1H-heptahydroazocin-2-on as an oil.

$^1$H-NMR spectrum (CDCl$_3$, δ ppm): 1.15 (3H, t, J=7 Hz), 1.4–1.7 (6H, m), 1.82 (2H, m), 2.48 (2H, m), 3.38 (2H, q, J=7 Hz), 3.47 (2H, m).

(2) Step 2:

To a solution of 25 g of the above product in 200 ml of chloroform, 34 g of phosphorus pentachloride was added portionwise under stirring and ice-cooling, followed by additional 30 minutes' stirring under the same conditions. To the resultant mixture 0.4 g of iodine was added under stirring and ice-cooling, and then 25 g of bromine was slowly added dropwise under the same conditions, followed by 2 hours' heating under reflux. The solvent was evaporated under reduced pressure. The residue was dissolved in ethyl acetate, washed successively with water and aqueous sodium thiosulfate solution, and dried over anhydrous magnesium sulfate, and the solvent was evaporated under reduced pressure. The residue was subjected to silica gel column chromatography, whereby eluted and purified with n-hexane-ethyl acetate (4:1). Thus obtained crytstallines were recrystallized form n-hexane to provide 10 g of a mixture of 3-bromo-1-ethyl-1H-heptahydroazocin-2-on and 3-chloro-1-ethyl-1H-heptahydroazocin-2-on.

(3) Step 3:

A mixture of 10 g of the above mixture, 12 g of sodium azide, 2.0 g of sodium iodide and 100 ml of dimethylformamide was stirred overnight at 80° C., poured into ice water, and extracted with diethyl ether. The extract was dried over anhydrous magnesium sulfate and the solvent was evaporated under reduced pressure. The resulting residue was subjected to silica gel column chromatography, whereby eluted and purified with n-hexane-ethyl acetate (4:1) to provide 4.8 g of 3-azide-1-ethyl-1H-hetahydroazocin-2-on as an oil.

$^1$H-NMR spectrum (CDCl$_3$, δ ppm): 1.18 (3H, t, J=7 Hz), 1.5–1.8 (6H, m), 2.2 (2H, m), 3.08 (1H, m), 3.28 (1H, m), 3.53 (1H, m), 3.76 (1H, m), 4.0 (1H, dd, J=10.5 Hz, J=5.6 Hz).

(4) Step 4:

To 36.4 g of a 70% toluene solution of sodium bis(2-methoxyethoxy)-aluminum hydride, 100 ml of toluene was added, and to the resulting solution further 4.8 g of the above product was gradually added under stirring and ice-cooling, followed by 2 hours' stirring at room temperature. To the reaction mixture, water and 48% aqueous sodium hydroxide solution were added gradually under stirring and ice-cooling, and the mixture was extracted with diethyl ether. The extract was dried over anhydrous magnesium sulfate and the solvent was evaporated under reduced pressure to provide 3.8 g of the title compound as an oil.

EXAMPLE 24 a reaction according to scheme 3

Preparation of 3-amino-1-ethyl-1H-octahydroazonine (1) To a solution of 17 g of 2-azacyclononanone and 29 g of ethane iodide in 200 ml of 1,2-dimethoxyethane, 6.0 g of 60% sodium hydride was gradually added under stirring at room temperature, followed by 4 hours' stirring under the same conditions. Then water was added to the mixture, followed by extraction with chloroform. The extract was washed with water, and dried over anhydrous magnesium sulfate, and the solvent was evaporated under reduced pressure to provide 20 g of 1-ethyl-1H-octahydroazonin-2-on as an oil.

(2) Step 1:

To 200 ml of a tetrahydrofuran solution containing 20 g of the above product, 78 ml of 2M lithium diisopropylamide in tetrahydrofuran was added dropwise under ice-cooling, followed by an hour's stirring. The reaction mixture was poured into dry ice, and the resultant mixture was diluted with water and washed with ethyl acetate. The aqueous layer was acidified with conc. hydrochloric acid, extracted with chloroform, washed with saturated aqueous sodium chloride solution, and dried over anhydrous magnesium sulfate. The solvent was evaporated under reduced pressure to give 14 g of 3-carboxy-1-ethyl-1H-octahydroazonin-2-on, m.p. 109–110° C. (recrystallized from diethyl ether-n-hexane).

(3) Step 2:

To 100 ml of an acetone solution containing 12 g of the above product, 12 ml of water and 7.0 ml of triethylamine were added. To the resultant mixture, 30 ml of an acetone solution containing 8.0 g of ethyl chloroformate was added dropwise with ice-cooling, followed by 30 minutes' stirring. Further 30 ml of an aqueous solution containing 6.1 g of sodium azide was added dropwise to the reaction mixture, which was then stirred for 1.5 hours. The reaction mixture was poured into ice water and extracted with diethyl ether. The extract was washed with saturated sodium chloride solution and dried over anhydrous magnesium sulfate. The solvent was evaporated under reduced pressure, and to the resultant residue 200 ml of toluene was added. The solution was stirred under heating at 70° C. until foaming ceased, and then the temperature was raised to 100° C. followed by 2 hours' stirring. After termination of the reaction, the solvent was evaporated under reduced pressure. To the resulting residue, 120 ml of 20% hydrochloric acid was added under stirring and ice-cooling, followed by 1.5 hours' reflux. The reaction mixture was washed with ethyl acetate, and the aqueous layer was basified with an excess of potassium carbonate and extracted with chloroform. The extract was washed with saturated aqueous sodium chloride solution and dried over anhydrous magnesium sulfate. The solvent was evaporated under reduced pressure to give 8.5 g of 3-amino-1-ethyl-1H-octahydroazonin-2-on was obtained as an oil.

(4) Step 3:

To a solution of 8.5 g of the above product in 100 ml of chloroform, 7.0 ml of triethylamine was added, and then 14 g of chlorotriphenylmethane was added portionwise under ice-cooling, followed by 3 hours' stirring at room temperature. The reaction mixture was washed with saturated aqueous sodium chloride solution, and dried over anhydrous magnesium sulfate, and the solvent was evaporated under reduced pressure. The residue was subjected to silica gel column chromatography, whereby eluted and purified with ethyl acetate-n-hexane (1:10) to provide 14 g of 3-triphenylmethylamino-1-ethyl-1H-octahydroazonin-2-on as a solid, m.p., 160–162° C. (recrystallized from n-hexane-ethyl acetate).

(5) Step 4:

To 30 g of a 70% toluene solution of sodium bis(2-methoxyethoxy)aluminum hydride, 100 ml of toluene was added, to which then 14 g of the above-obtained product was gradually added under stirring and ice-cooling. The mixture was stirred for overnight at room temperature. After cooling the reaction mixture, 2N aqueous sodium hydroxide solution was added dropwise to the reaction mixture, and further 48% aqueous sodium hydroxide solution was added. The solution was extracted with ethyl acetate. The extract was washed successively with water and saturated aqueous sodium chloride solution, dried over anhydrous magnesium sulfate and the solvent was evaporated under reduced pressure. The residue was subjected to silica gel column chromatography, whereby eluted and purified with ethyl acetate-n-hexane (1:10) to give 13 g of 3-triphenylmethylamino-1-ethyl-1H-octahydroazonine.

(6) Step 5:

To a mixture of 13 g of the above product and 3 ml of tetrahydrofuran, 45 ml of 10% hydrochloric acid was added, followed by 5 hours' stirring at room temperature. The reaction mixture was washed with diethyl ether. The aqueous layer was basified with an excess amount of potassium carbonate and extracted with chloroform. The extract was dried over anhydrous magnesium sulfate, and the solvent was evaporated under reduced pressure to give 5.0 g of the title compound as an oil.

Referential Example 1
a reaction according to step 1 of scheme 4
Preparation of 4-chloro-N-(1-ethyl-1H-hexahydroazepin-3-yl)-2-methoxy-5-nitrobenzamide To a suspension of 14.7 g of 4-chloro-2-methoxy-5-nitrobenzoic acid, 300 ml of chloroform and 1 ml of dimethylformamide, 22.7 g of thionyl chloride was added, and the mixture was heated for an hour under reflux. After termination of the reaction, the solvent was evaporated under reduced pressure and the residue was dissolved in 200 ml of methylene chloride, to which 12.9 g of triethylamine and 9.0 g of 3-amino-1-ethyl-1H-hexahydroazepine were added under ice-cooling, followed by 15 hours' stirring at room temperature. The reaction mixture was washed successively with water and saturated aqueous sodium chloride solution, and dried over anhydrous magnesium sulfate, and the solvent was evaporated under reduced pressure. The residue was subjected to silica gel column chromatography, whereby eluted and purified with chloroform-methanol (9:1) to provide 9.8 g of the title compound as a solid.

Referential Example 2
a reaction according to step 1 of scheme 4
Preparation of (R)-4-chloro-N-(1-ethyl-1H-hexahydroazepin-3-yl)-2-methoxy-5-nitrobenzamide Referential Example 1 was repeated except that (R)-3-amino-1-ethyl-1H-hexahydroazepine was used. The title compound was obtained as a solid.

Referential Example 3
a reaction according to step 1 of scheme 4
Preparation of (S)-4-chloro-N-(1-ethyl-1H-hexahydroazepin-3-yl)-2-methoxy-5-nitrobenzamide Referential Example 1 was repeated except that (S)-3-amino-1-ethyl-1H-hexahydroazepine was used. The title compound was obtained as a solid.

Referential Example 4
reactions according to steps 2 and 3 of scheme 4
Preparation of 5-amino-N-(1-ethyl-1H-hexahydroazepin-3-yl)-2-methoxy-4-methylaminobenzamide (1) Step 2:

To 100 ml of an ethanol solution containing 4.9 g of 4-chloro-N-(1-ethyl-1H-hexahydroazepin-3-yl)-2-methoxy-5-nitrobenzamide, 50 ml of 30% methylamine ethanol solution was added, followed by 1.5 hours' heating under reflux. The solvent was evaporated under reduced pressure, and water was added to the remaining residue. The crystallines were collected by filtration, washed with water and dried to provide 3.6 g of N-(1-ethyl-1H-hexahydroazepin-3-yl)-2-methoxy-4-methylamino-5-nitrobenzamide.

(2) Step 3:

3.3 Grams of the above product was dissolved in 200 ml of 20% hydrous methanol. To the solution 10% palladium-on-carbon was added, and the mixture was hydrogenated at atmospheric pressure and room temperature. After the theoretical amount of hydrogen was absorbed, the palladium-on-carbon was removed by filtration and the methanol in the filtrate was evaporated under reduced pressure. Thus an aqueous solution containing the title compound was obtained.

Referential Example 5
reactions according to steps 2 and 3 of scheme 4
Preparation of (R)-5-amino-N-(1-ethyl-1H-hexahydroazepin-3-yl)-2-methoxy-4-methylaminobenzamide (2) Step 2:

To 600 ml of an ethanol solution containing 56.8 g of (R)-4-chloro-N-(1-ethyl-1H-hexahydroazepin-3-yl)-2-methoxy-5-nitrobenzamide, 300 ml of 40% methylamine aqueous solution was added, followed by 2 hours' heating under reflux. The solvent was evaporated under reduced pressure, and the crystalline precipitates obtained were collected by filtration. The precipitates were washed with water and dried to provide 32 g of (R)-N-(1-ethyl-1H-hexahydroazepin-3-yl)-2-methoxy-4-methylamino-5-nitrobenzamide.

(2) Step 3:

To 33.2 g of the above product 200 ml of methanol, 400 ml of water, 80 ml of acetic acid and 2.0 g of 10% palladium-on-carbon were added, and the mixture was hydrogenated at atmospheric pressure and room temperature. After the theoretical amount of hydrogen was absorbed, the palladium-on-carbon was removed by filtration, and the methanol in the filtrate was evaporated under reduced pressure. Thus an aqueous acetic acid solution containing the title compound was obtained.

Referential Examples 6–8
reactions according to steps 2 and 3 of scheme 4
Preparation of 4-substituted amino-5-amino-N-(1-ethyl-1H-hexahydroazepin-3-yl)-2-methoxy-benzamide or its optical isomers Using 4-chloro-N-(1-ethyl-1H-hexahydroazepin-3-yl)-2-methoxy-5-nitrobenzamides having the same configuration with that of the final products and the corresponding amines, reactions and treating were conducted in the manner similar to Referential Example 5, to provide aqueous solutions of the compounds listed in Table 7.

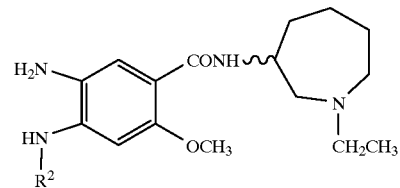

TABLE 7

| Referential Example | configuration | R² |
|---|---|---|
| 6 | S | Me |
| 7 | RS | Et |
| 8 | R | Et |

Referential Example 9
reactions according to steps 2 and 3 of scheme 4
Preparation of 5-amino-4-benzylamino-N-(1-ethyl-1H-hexahydroazepin-3-yl)-2-methoxybenzamide (1) Step 2:

To 50 ml of an ethanol solution containing 2.0 g of 4-chloro-N-(1-ethyl-1H-hexahydroazepin-3-yl)-2-methoxy-5-nitrobenzamide, 6.0 g of benzylamine was added, and heated under reflux for 22 hours. The solvent was evaporated under reduced pressure. Water was added to the residue, followed by extraction with chloroform. The extract was washed with saturated aqueous sodium chloride solution, and dried over anhydrous sodium sulfate and the solvent was evaporated under reduced pressure. The residue was subjected to silica gel column chromatography, whereby eluted and purified with chloroform-methanol (12:1) to provide 2.4 g of 4-benzylamino-N-(1-ethyl-1 H-hexahydroazepin-3-yl)-2-methoxy-5-nitrobenzamide as a solid.

(2) Step 3:

To 1.6 g of the above product, (6 ml of conc. hydrochloric acid and 3 ml of ethanol were added. Then further a solution of 2.6 g of stannous chloride.dihydrate in 3 ml of an ethanol was added, followed by an hour's stirring at 80° C. After termination of the reaction, ethanol was evaporated under reduced pressure to provide an aqueous hydrochloric acid solution containing the title compound.

Referential Example 10
Preparation of 6-methoxy-1-methyl-1H-benzotriazole-5-carboxylic acid [a compound of formula (III) in which $R^{2a}$ is methyl group]

(1) Referential Example 1 was repeated except that the 3-amino-1-ethyl-1H-hexahydroazepine was replaced by propylamine. Thus 4-chloro-2-methoxy-5-nitro-N-propylbenzamide was obtained as a solid.

(2) 4-chloro-N-(1-ethyl-1H-hexahydroazepin-3-yl)-2-methoxy-5-nitrobenzamide used in Referential Example 4 (1) was replaced by the above product, and the reaction and treating were carried out in the manner similar to Referential Example 4. Thus 5-amino-2-methoxy-4-methylamino-N-(1-propyl)benzamide was obtained as a solid.

(3) 5-amino-N-(1-ethyl-1H-hexahydroazepin-3-yl)-2-methoxy-4-methylaminobenzamide used in Example 1 was replaced by the above product. The reaction and treating were conducted in the manner similar to Example 1 to provide 6-methoxy-1-methyl-N-(1-propyl)-1H-benzotriazole-5-carboxamide as a solid.

(4) A mixture of 6.9 g of the above product and 100 ml of conc. hydrochloric acid was heated under reflux for 5.5 hours. The reaction mixture was cooled and concentrated under reduced pressure. The resulting crystalline precipitates were collected by filtration, washed with water and dried to give 3.2 g of the title compound.

Formulation Example 1
Preparation of tablets (per 1,000 tablets)

| | |
|---|---|
| (R)-N-(1-ethyl-1H-hexahydroazepin-3-yl)-6-methoxy-1-methyl-1H-benzotriazole-5-carboxamide (Compound 2) | 5 g |
| Lactose | 80 g |
| Corn starch | 30 g |
| Microcrystalline cellulose | 25 g |
| Hydroxypropylcellulose | 3 g |
| Light silicic anhydride | 0.7 g |
| Magnesium stearate | 1.3 g |

The above components were mixed and granulated in the conventional manner and tableted to give 1,000 tablets (145 mg/tablet)

Formulation Example 2
Preparation of capsules (per 1,000 capsules)
(R)-N-(1-ethyl-1H-hexahydroazepin-3-yl)-6-methoxy-1H-benzotriazole-5-carboxamide.3/2

| | |
|---|---|
| fumarate (Compound 7b) | 10 g |
| Lactose | 160 g |
| Corn starch | 22 g |
| Hydroxypropylcellulose | 3.5 g |
| Light silicic anhydride | 1.8 g |
| Magnesium stearate | 2.7 g |

The above components were mixed and granulated in the conventional manner and filled into 1,000 capsules.

Formulation Example 3
Preparation of powder
(R)-N-(1-ethyl-1H-hexahydroazepin-3-yl)-6-methoxy-1H-benzotriazole-5-carboxamide.3/2

| | |
|---|---|
| fumarate (Compound 7b) | 40 g |
| Lactose | 960 g |
| Hydroxypropylcellulose | 25 g |
| Light silicic anhydride | 5 g |

The above components were mixed and formulated into a powder preparation in the conventional manner.

Formulation Example 4
Preparation of an injection (per 1,000 ampoules)
(R)-N-(1-ethyl-1H-hexahydroazepin-3-yl)-6-methoxy-1H-benzotriazole-5-carboxamide.3/2

| | |
|---|---|
| fumarate (Compound 7b) | 10 g |
| Sorbitol | 100 g |
| Water for injection | q.s. |
| Total | 2,000 ml |

(R)-N-(1-ethyl-1H-hexahydroazepin-3-yl)-6-methoxy-1H-benzotriazole-5-carboxamide.3/2 fumarate and sorbitol were dissolved in a part of water for injection. To the solution the remainder of water for injection was added to give total amount. The above solution was filtered by membrane filter (0.22 μm). The filtrate was filled in 2 ml ampoules and sterilized at 121° C. for 20 minutes.

Industrial Applicability

As so far explained, the compounds of the present invention which are represented by the formula (I) and their pharmaceutically acceptable acid addition salts exhibit concurrently excellent antiemetic activity and gastrointestinal motility enhancing activity, while processing less CNS depressant activity and, therefore, are useful as gastrointestinal motility improving agents for the treatments and prophylaxis of various functional disorders of gastrointestinal tract, which are associated with various diseases and their therapy. The intermediates of the present invention which are represented by formula (II) are useful as synthetic intermediates for the compounds of formula (I) in which $R^2$ is a hydrogen atom. Also the intermediates of the present invention which are represented by formula (IVa) are useful as synthetic intermediates for the compounds of formula (I) whose configuration is R.

We claim:

1. An (R)-N-(1-ethyl-1H-hexahydroazepin-3-yl)-6-methoxy-1H-benzotriazole-5-carboxamide derivative which is represented by the formula (I) below:

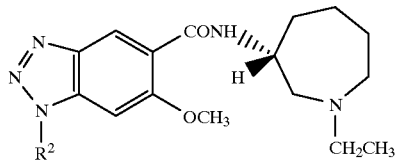

(I)

in which $R^2$ represents hydrogen atom or methyl group, or its pharmaceutically acceptable acid addition salt.

2. (R)-N-(1-ethyl-1H-hexahydroazepin-3-yl)-6-methoxy-1H-benzotriazole-5-carboxamide or a pharmaceutically acceptable acid addition salt thereof.

3. (R)-N-(1-ethyl-1H-hexahydroazepin-3-yl)-6-methoxy-1-methyl-1H-benzotriazole-5-carboxamide or a pharmaceutically acceptable acid addition salt thereof.

4. A pharmaceutical composition which comprises a pharmaceutically effective amount of an (R)-N-(1-ethyl-1H-hexahydroazepin-3-yl)-6-methoxy-1H-benzotriazole-5-carboxamide derivative which is represented by the formula (I) below:

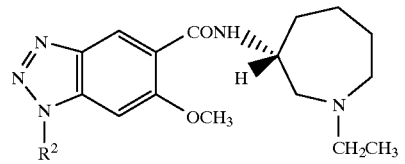

(I)

in which $R^2$ represents hydrogen atom or methyl group, or its pharmaceutically acceptable acid addition salt, and a pharmaceutically acceptable carrier.

5. A pharmaceutical composition having anti-emetic activity and gastrointestinal motility enhancing activity according to claim 4, which comprises a pharmaceutically effective amount of an (R)-N-(1-ethyl-1H-hexahydroazepin-3-yl)-6-methoxy-1H-benzotriazole-5-carboxamide derivative represented by the formula (I) or its pharmaceutically acceptable acid addition salt, and a pharmaceutically acceptable carrier.

6. A pharmaceutical composition having anti-emetic activity and gastrointestinal motility enhancing activity according to claim 4, which comprises a pharmaceutically effective amount of an (R)-N-(1-ethyl-1H-hexahydroazepin-3-yl)-6-methoxy-1H-benzotriazole-5-carboxamide or a pharmaceutically acceptable acid addition salt thereof, and a pharmaceutically acceptable carrier.

7. A pharmaceutical composition having anti-emetic activity and gastrointestinal motility enhancing activity according to claim 4, which comprises a pharmaceutically effective amount of an (R)-N-(1-ethyl-1H-hexahydroazepin-3-yl)-6-methoxy-1-methyl-1H-benzotriazole-5-carboxamide or a pharmaceutically acceptable acid addition salt thereof, and a pharmaceutically acceptable carrier.

* * * * *